United States Patent
Keane

(10) Patent No.: US 10,080,660 B2
(45) Date of Patent: Sep. 25, 2018

(54) IMPLANTABLE INTRACARDIAC DEVICE AND METHODS THEREOF

(71) Applicant: PARADOX MEDICAL LIMITED, Dublin (IE)

(72) Inventor: David Keane, Dublin (IE)

(73) Assignee: Paradox Medical Limited, Dublin (IE)

( * ) Notice: Subject to any disclaimer, the term of this patent is extended or adjusted under 35 U.S.C. 154(b) by 4 days.

(21) Appl. No.: 14/976,785

(22) Filed: Dec. 21, 2015

(65) Prior Publication Data

US 2016/0220371 A1   Aug. 4, 2016

Related U.S. Application Data

(60) Provisional application No. 62/094,494, filed on Dec. 19, 2014.

(51) Int. Cl.
*A61F 2/24* (2006.01)

(52) U.S. Cl.
CPC .............. *A61F 2/2454* (2013.01); *A61F 2/24* (2013.01); *A61F 2/2442* (2013.01); *A61F 2220/0016* (2013.01)

(58) Field of Classification Search
CPC ........ A61F 2/24; A61F 2/2442; A61F 2/2454; A61F 2/2463; A61F 2220/0016; A61F 2230/0091
USPC ................................................ 623/2.36–2.37
See application file for complete search history.

(56) References Cited

U.S. PATENT DOCUMENTS

| | | | |
|---|---|---|---|
| 2005/0038509 A1* | 2/2005 | Ashe | A61F 2/2454 623/2.36 |
| 2007/0061010 A1 | 3/2007 | Hauser et al. | |
| 2008/0086164 A1 | 4/2008 | Rowe | |
| 2010/0298929 A1* | 11/2010 | Thornton | A61B 17/00234 623/2.1 |
| 2011/0066235 A1* | 3/2011 | Ferrazzi | A61B 17/00234 623/2.37 |

(Continued)

FOREIGN PATENT DOCUMENTS

| | | |
|---|---|---|
| JP | 2014-506175 A | 3/2014 |
| WO | WO 02/087481 A1 | 11/2002 |
| WO | WO 2009/070074 A1 | 6/2009 |

OTHER PUBLICATIONS

European Search Report for corresponding EP Application No. 14199443.4, dated Apr. 22, 2015, (6 pages).

*Primary Examiner* — Paul Prebilic
(74) *Attorney, Agent, or Firm* — Bookoff McAndrews, PLLC

(57) ABSTRACT

An implantable intracardiac device to prevent systolic anterior motion of the anterior mitral valve leaflet into the left ventricular outflow tract is described. The device comprises a blocking member configured for implantation within the left ventricle of the heart and in-situ blocking of systolic anterior motion of the mitral valve into the left ventricular outflow tract when anchored into the left ventricle of the heart. The device may be configured for radial expansion from a contracted orientation suitable for transluminal delivery to the left ventricle of the heart within a suitable delivery vehicle and an expanded orientation suitable for deployment within the left ventricle of the heart. The device comprises anchors configured for anchoring the device in-situ within the left ventricle to a wall of the left ventricle.

22 Claims, 33 Drawing Sheets

(56) References Cited

U.S. PATENT DOCUMENTS

2014/0100596 A1     4/2014   Rudman et al.
2015/0182335 A1     7/2015   Agyemang \* cited by examiner

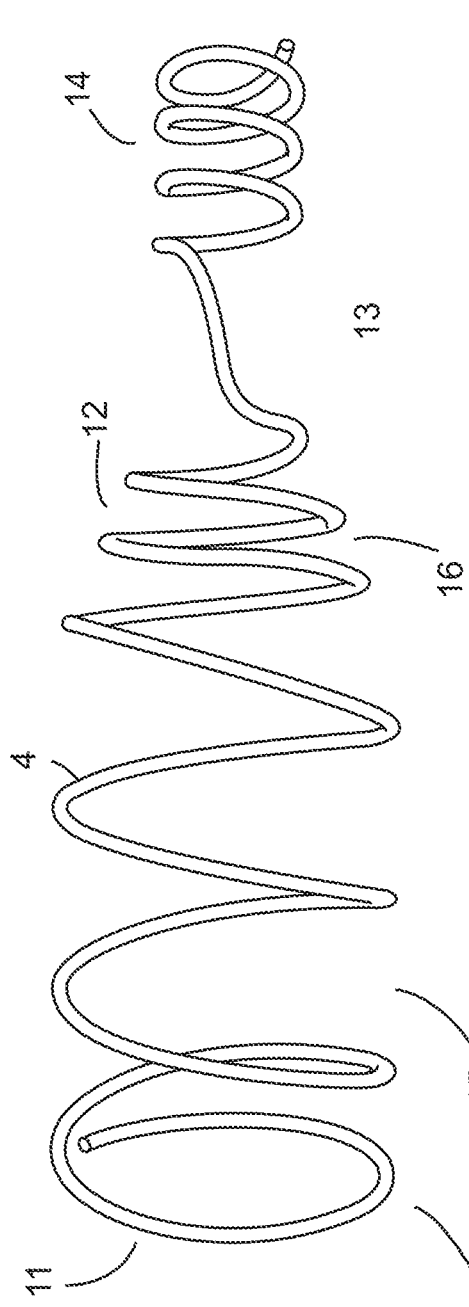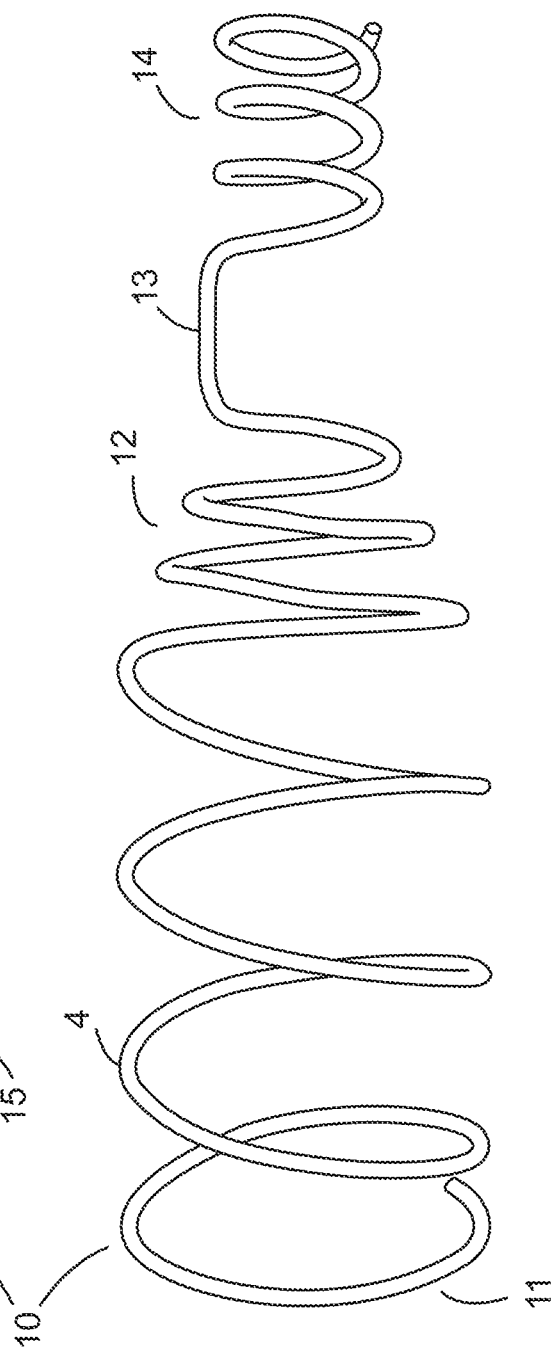

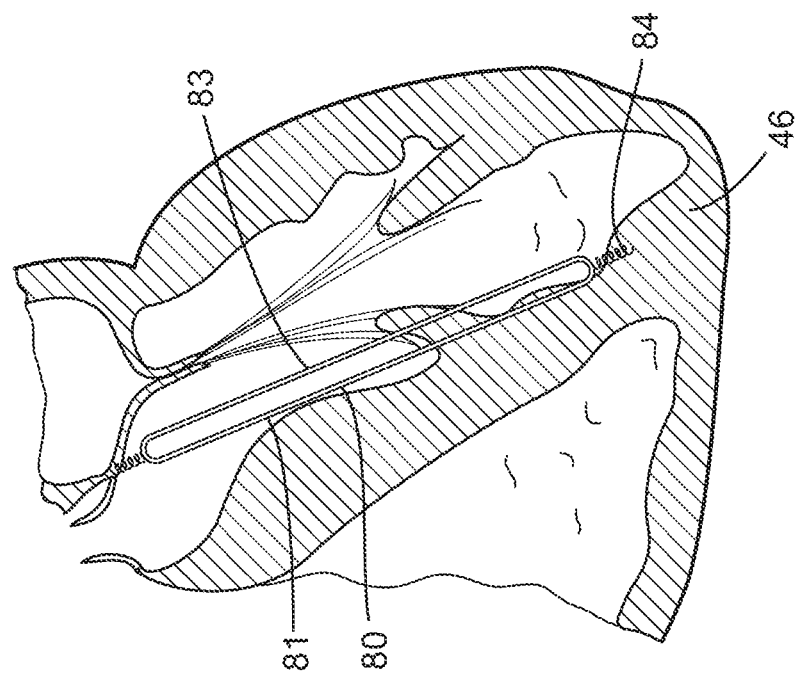
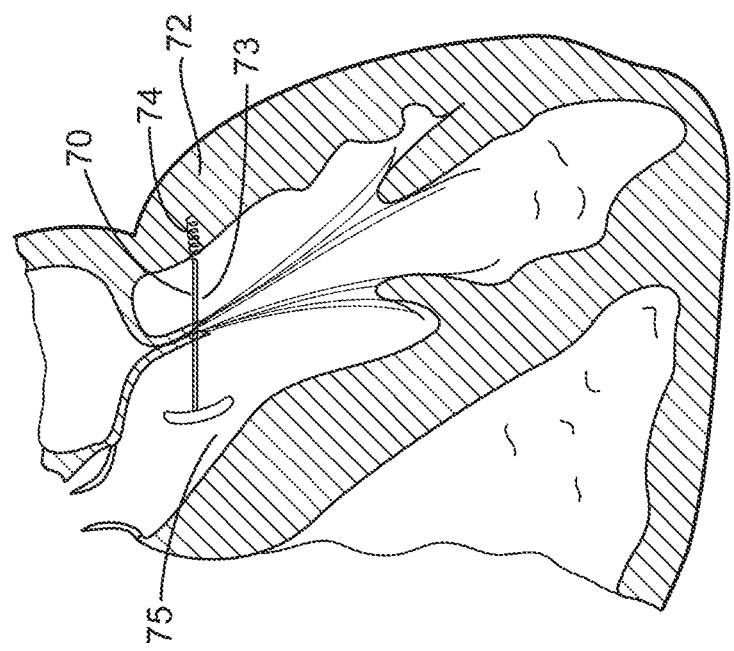
Fig. 11
Fig. 12

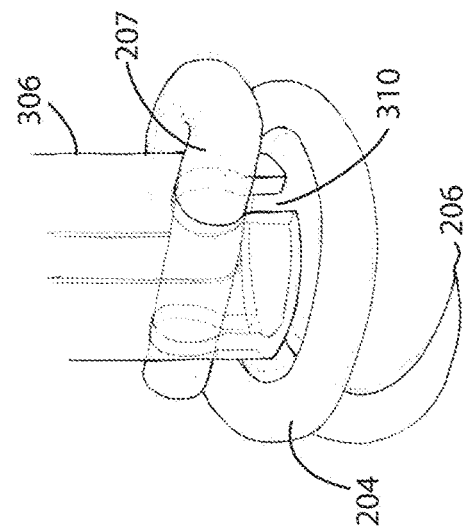
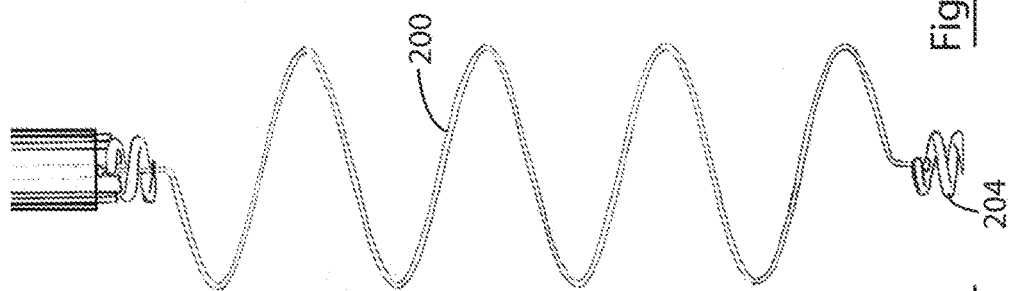
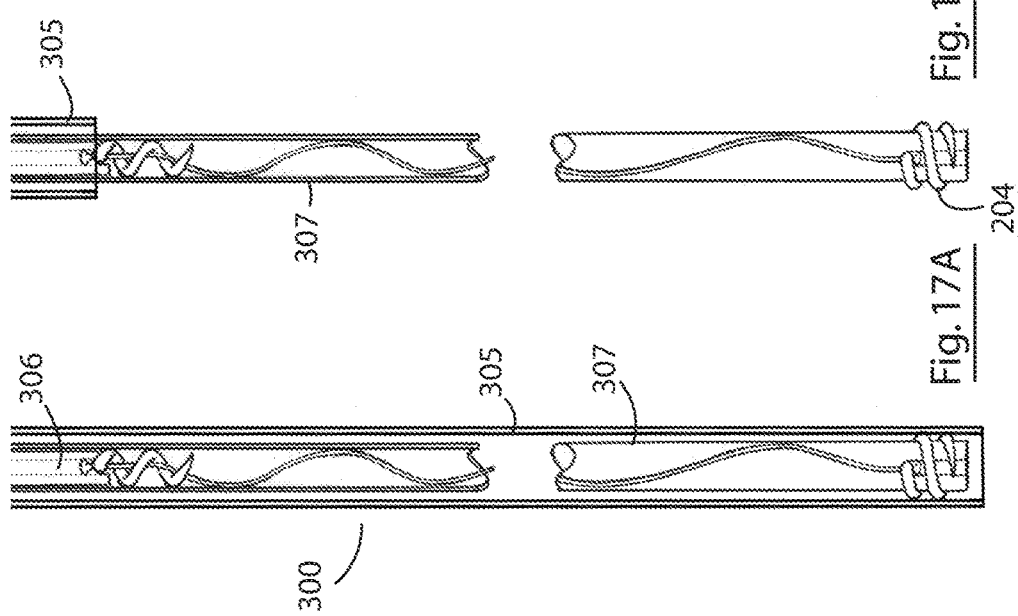

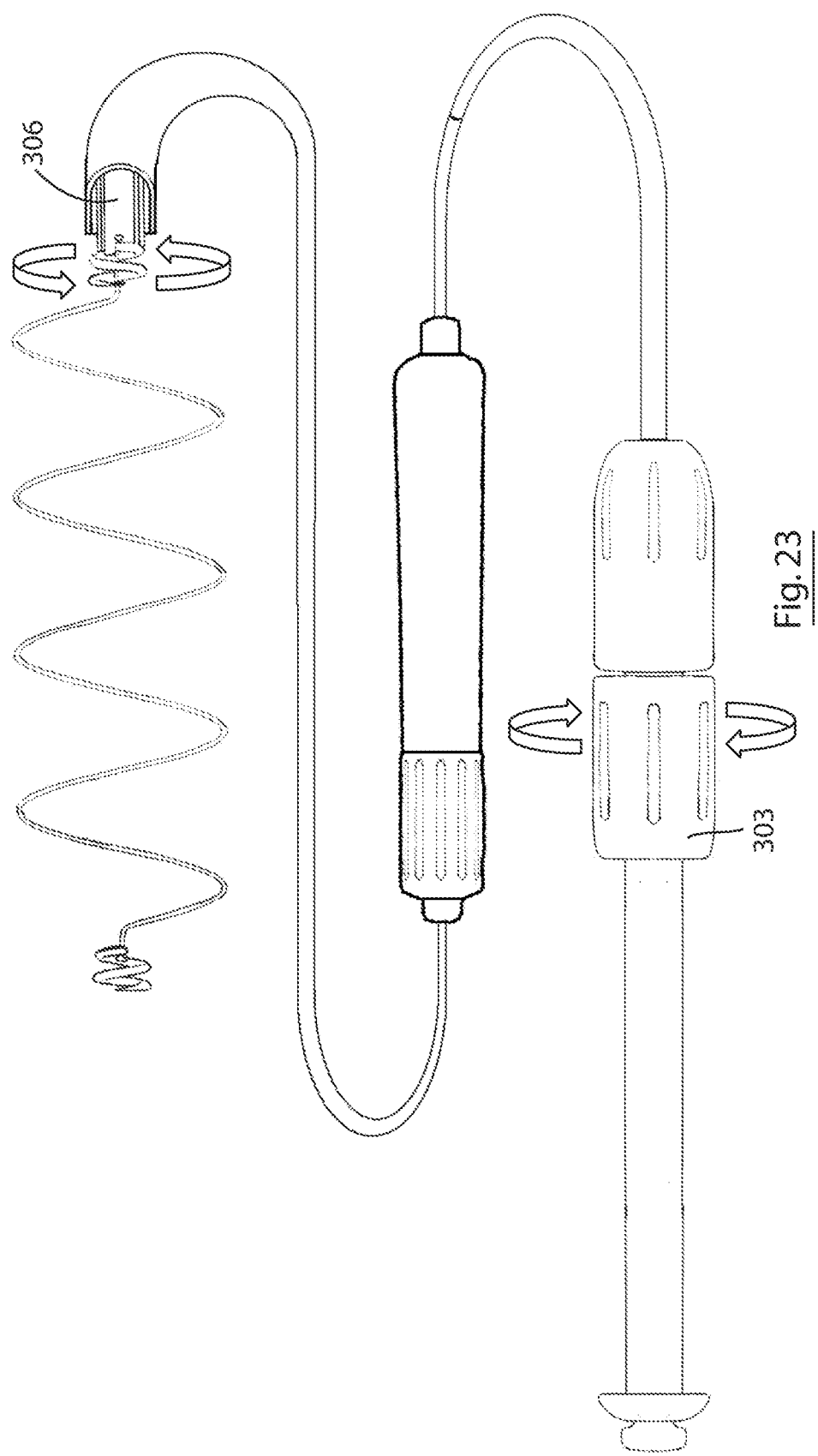

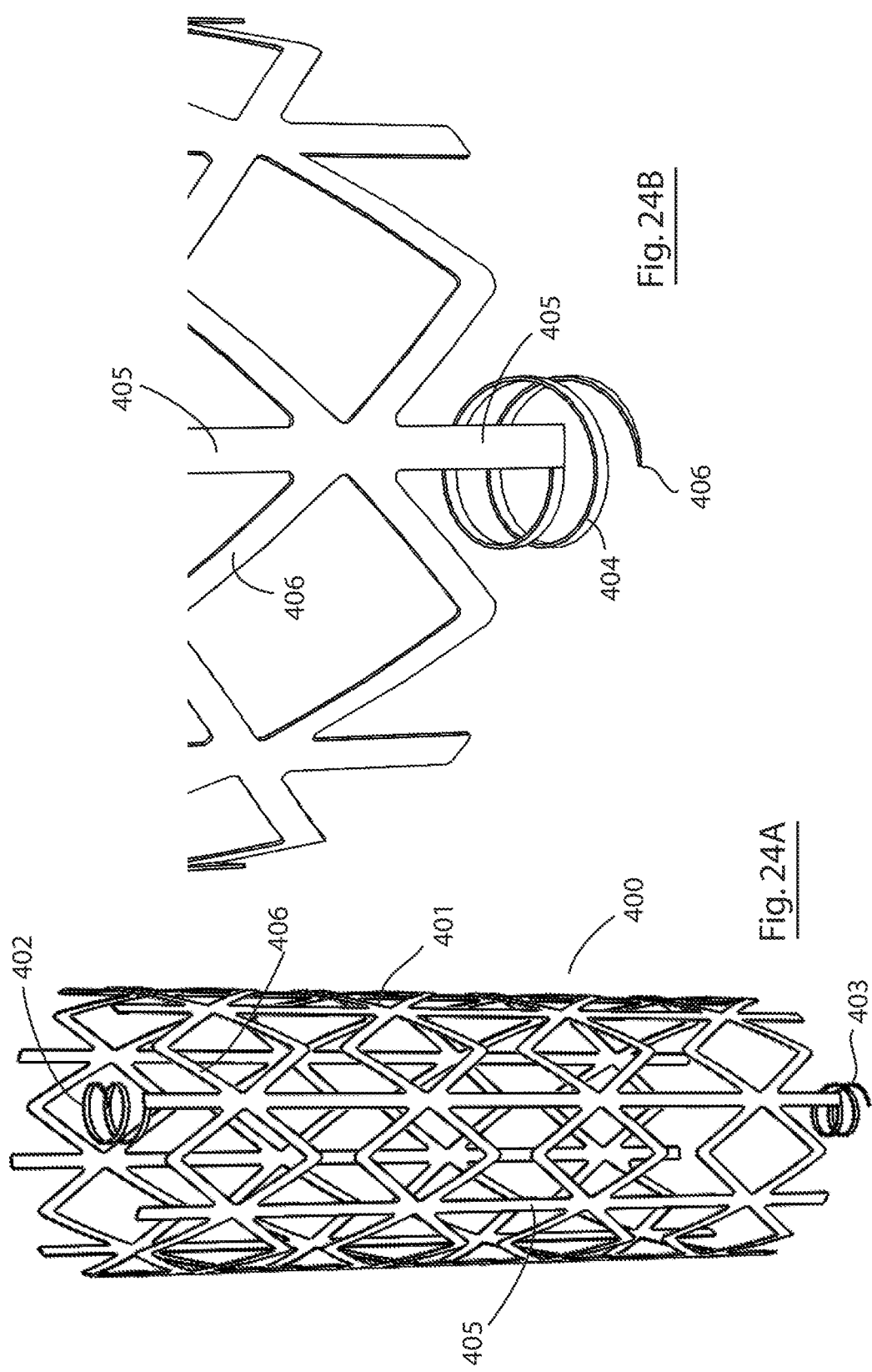

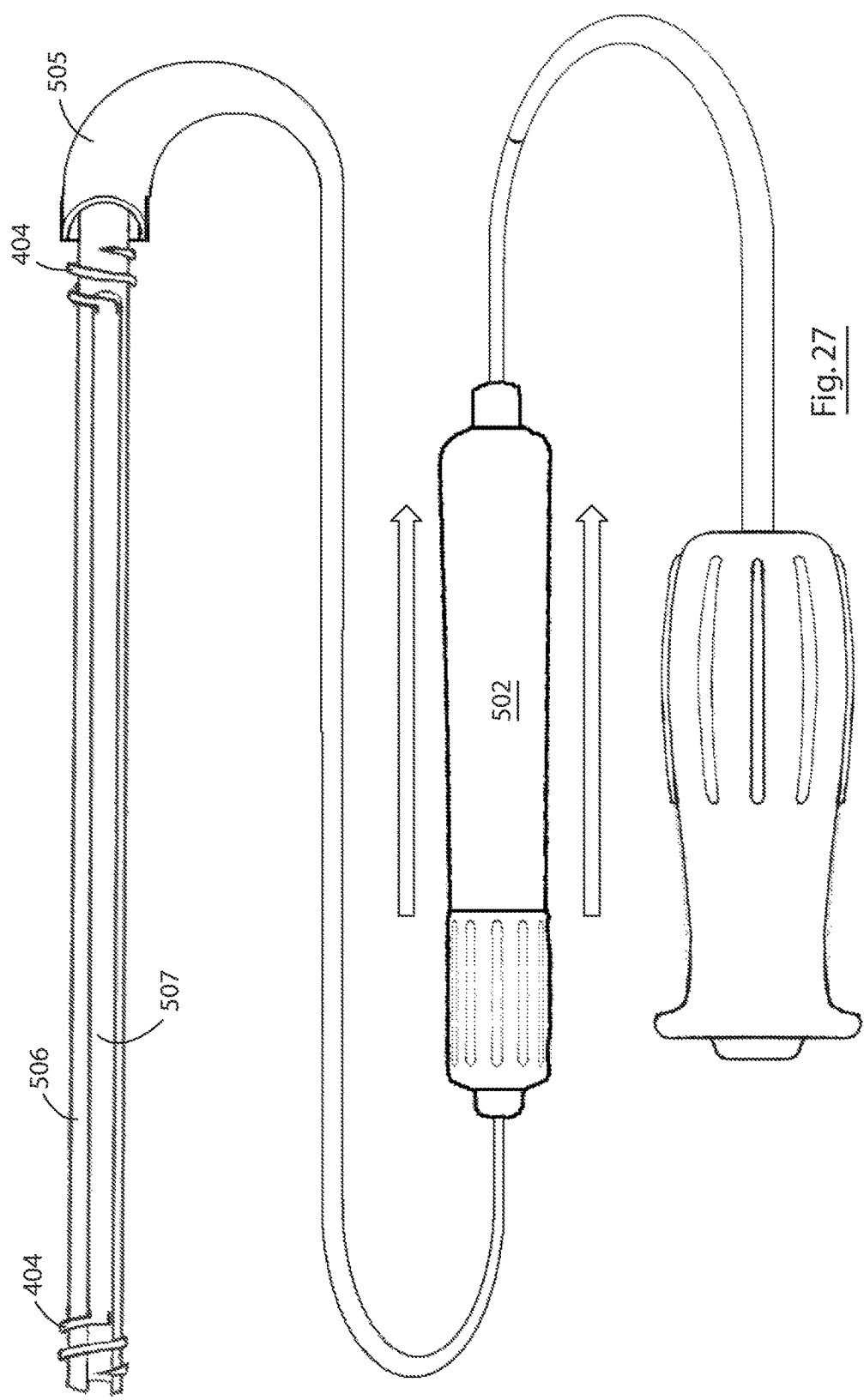

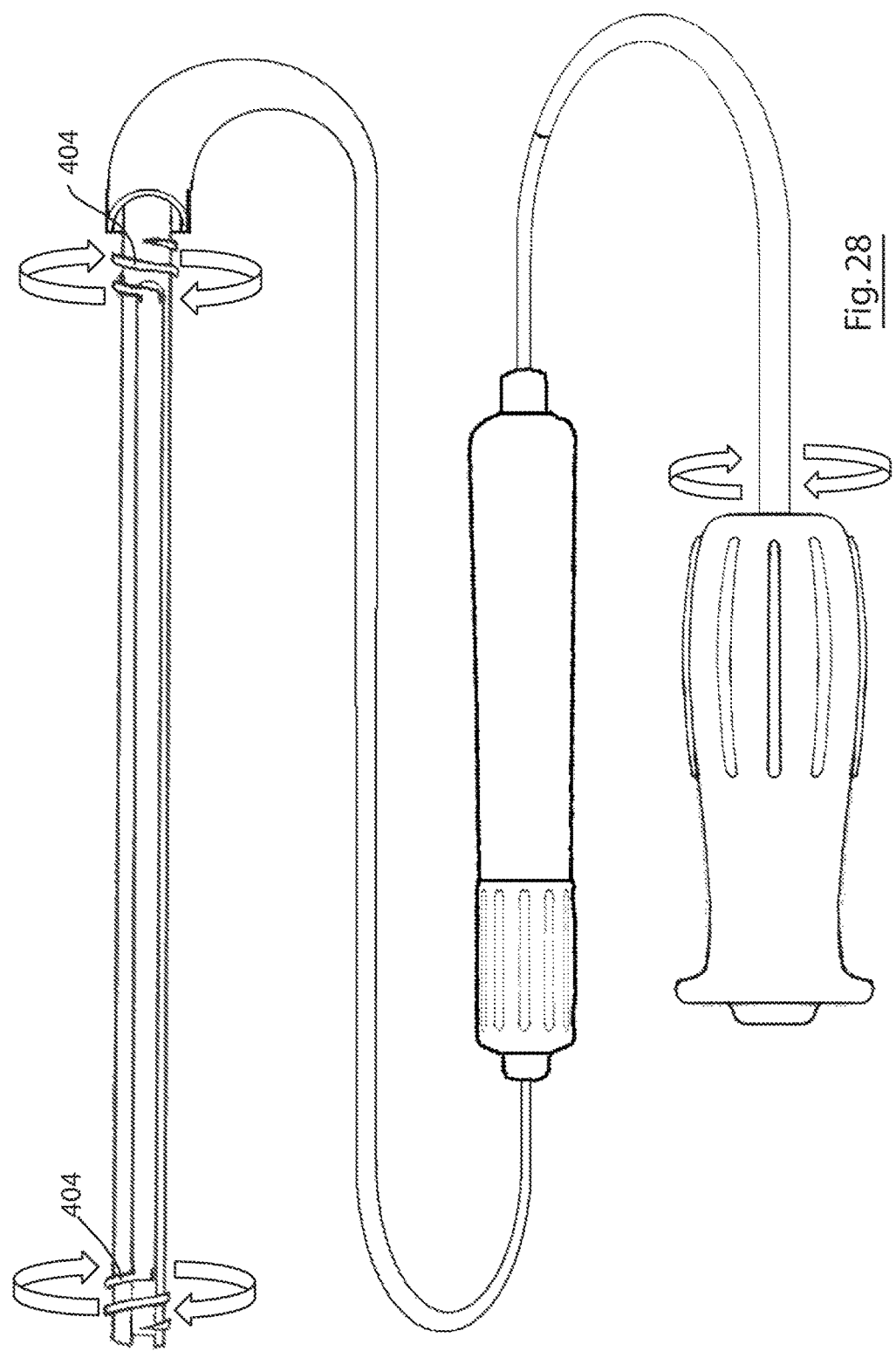

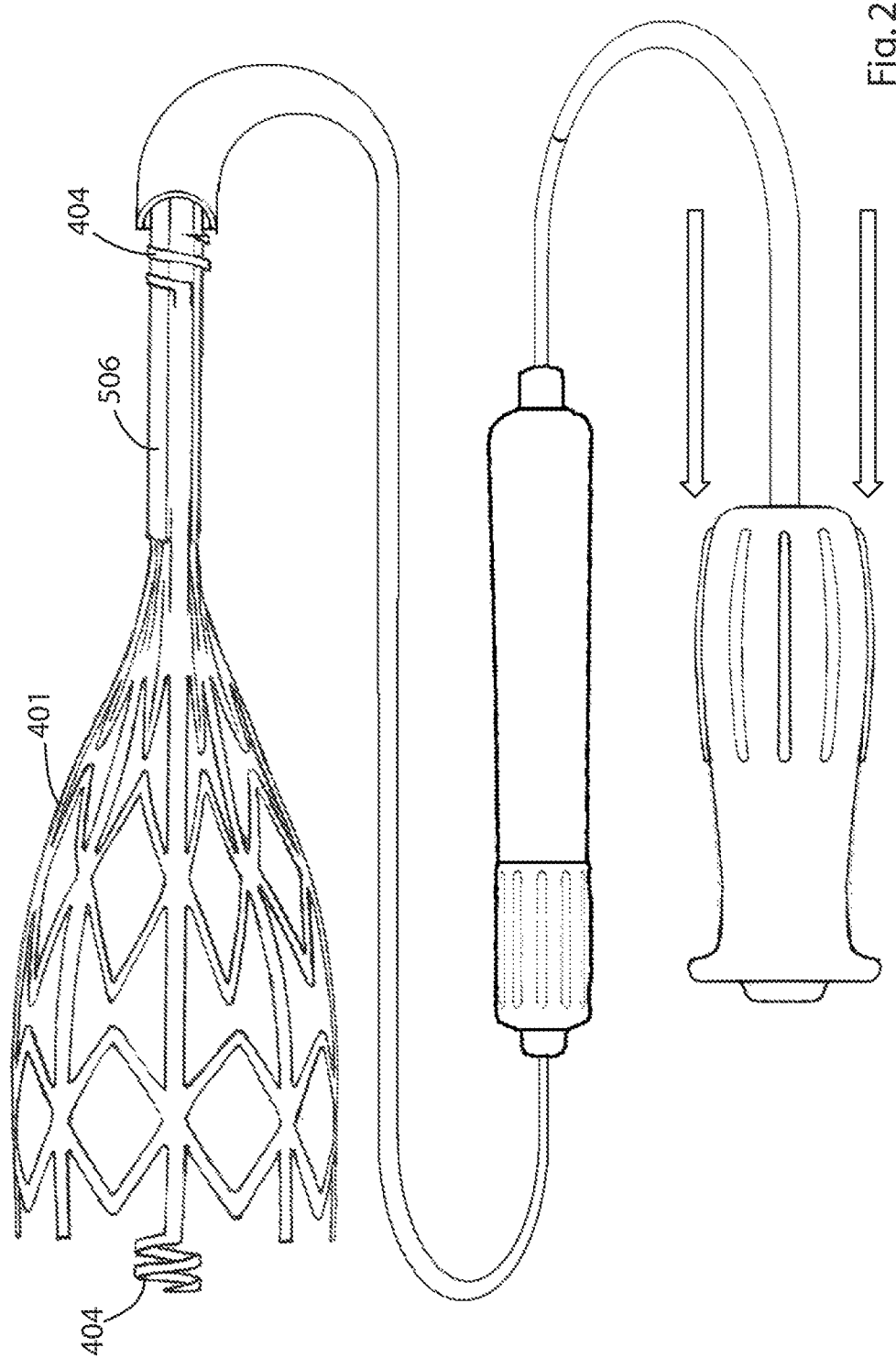

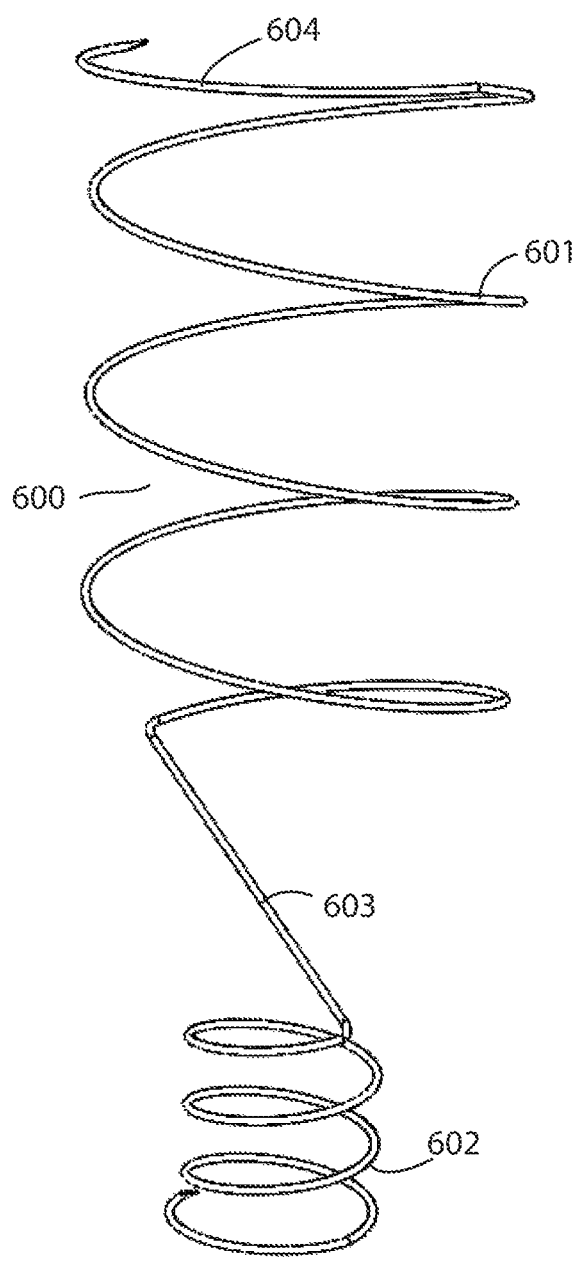
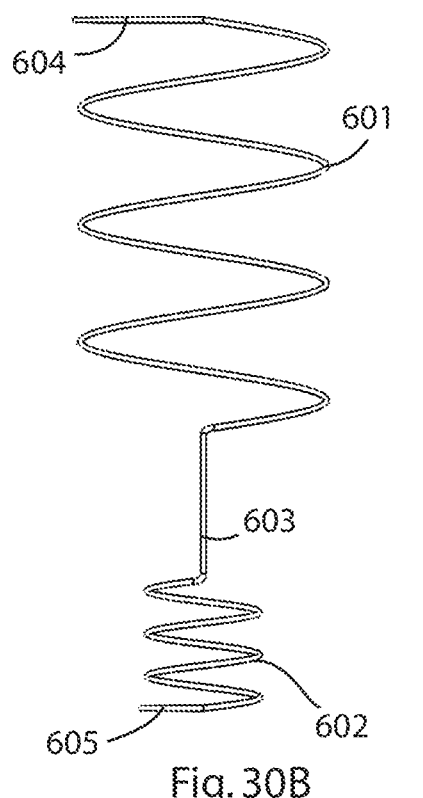
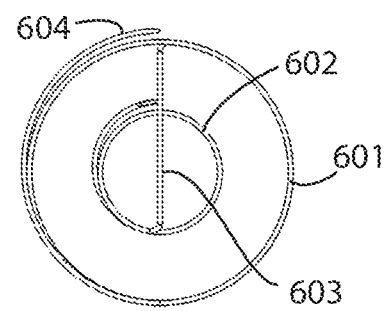
Fig. 30A
Fig. 30B
Fig. 30C

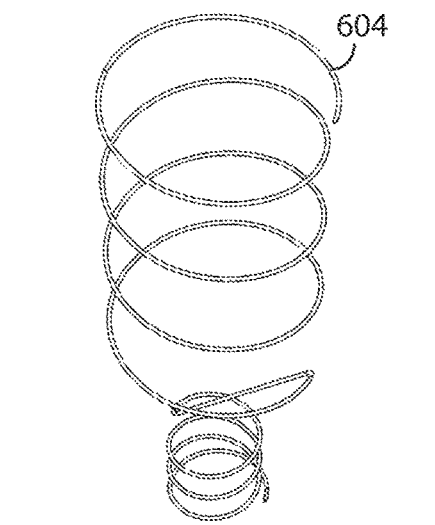
Fig. 31B
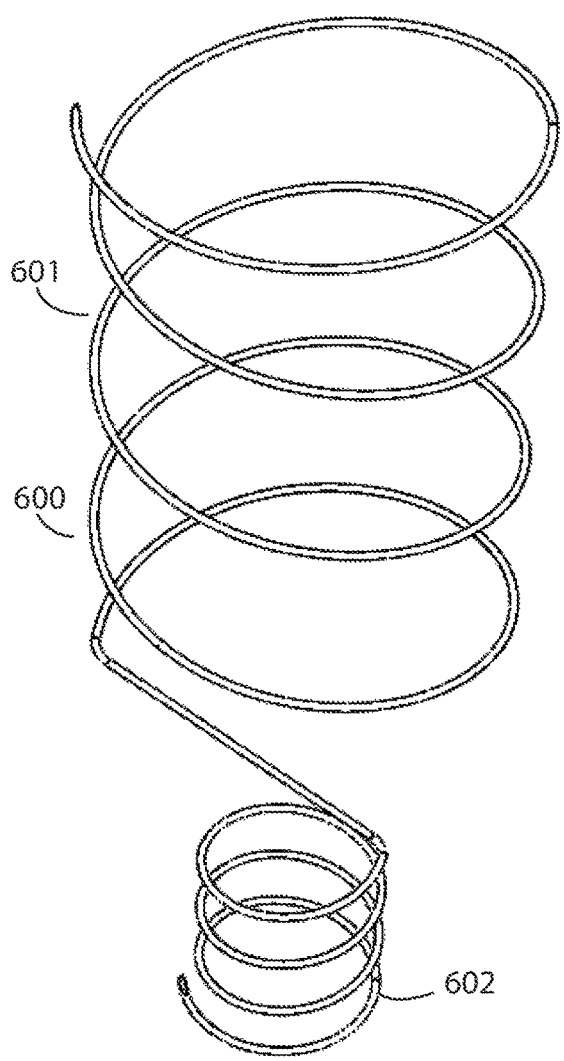
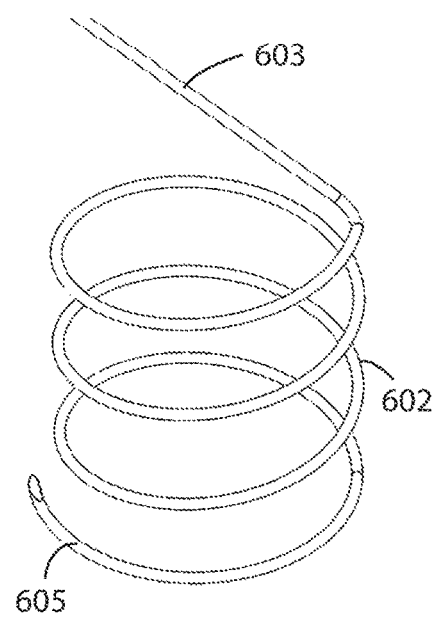
Fig. 31A
Fig. 31C

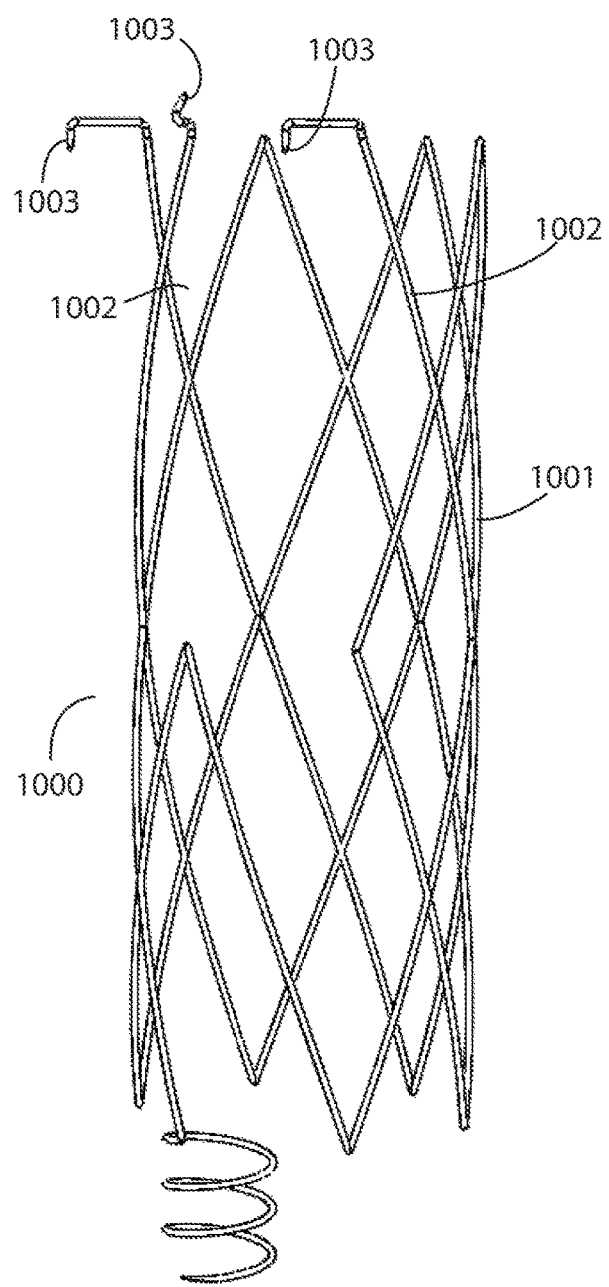
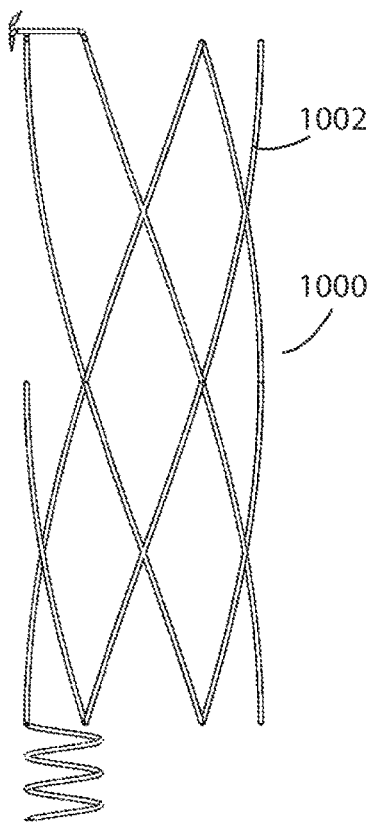
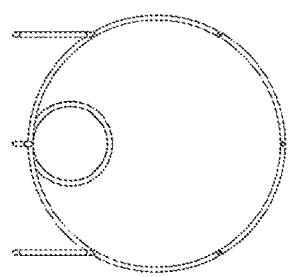
Fig. 36A
Fig. 36B
Fig. 36C

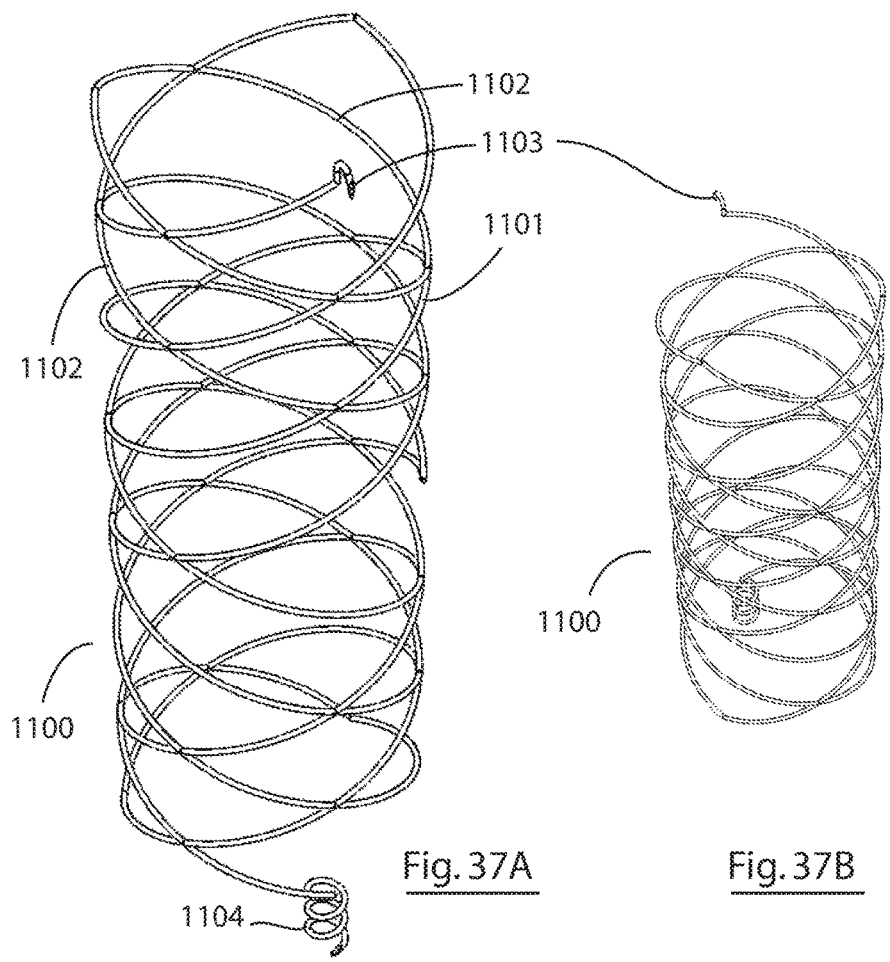
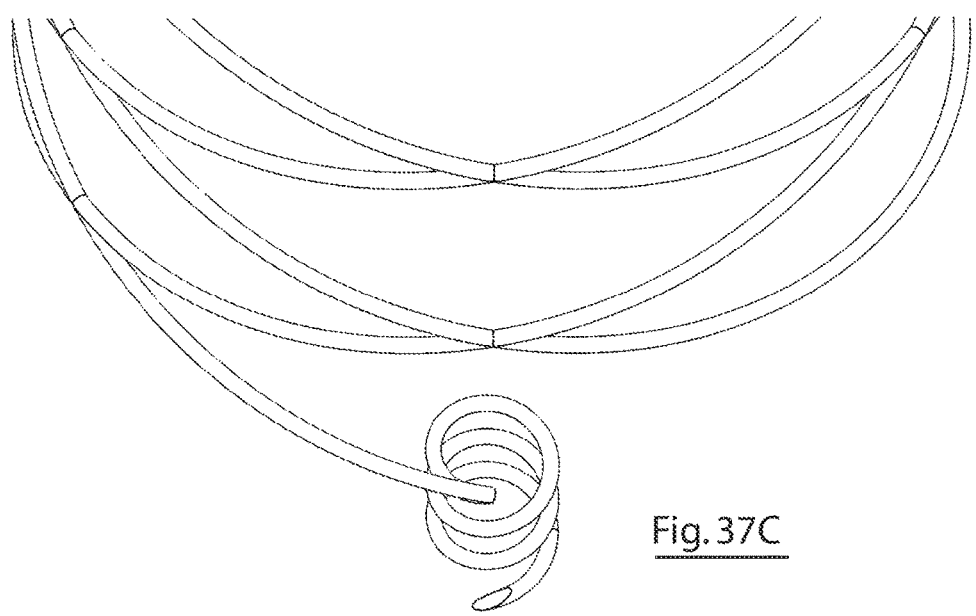
Fig. 37A  Fig. 37B
Fig. 37C

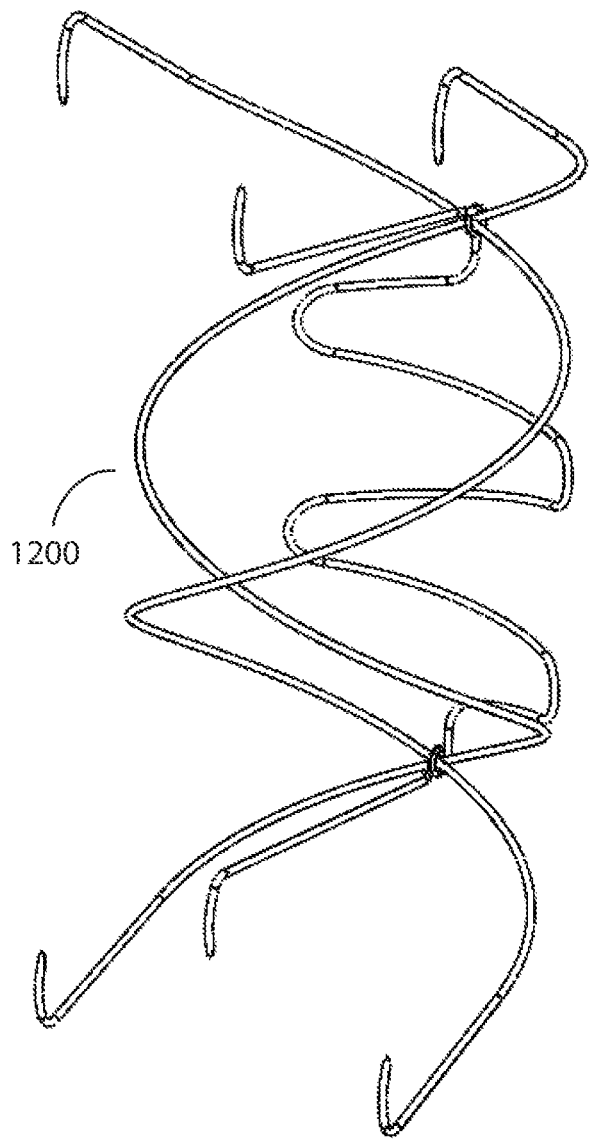
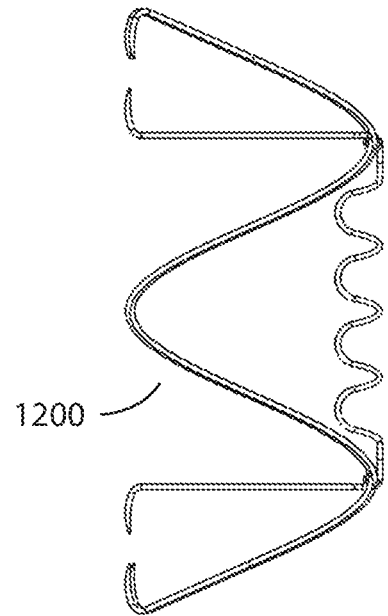
Fig. 39B
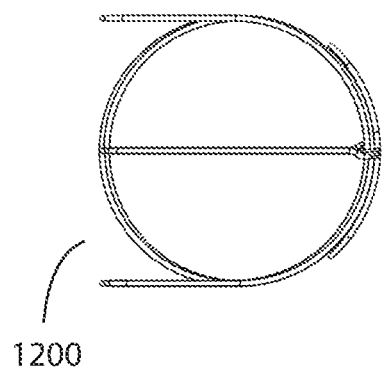
Fig. 39A	Fig. 39C

IMPLANTABLE INTRACARDIAC DEVICE AND METHODS THEREOF

CROSS-REFERENCE TO RELATED APPLICATIONS

This application claims the benefit of priority to U.S. Provisional Patent Application No. 62/094,494, filed on Dec. 19, 2014, the entire contents of which is herein incorporated by reference.

BACKGROUND TO THE INVENTION

Hypertrophic cardiomyopathy is found in 1:500 people. In patients with hypertrophic obstructive cardiomyopathy (HOCM), left ventricular outflow tract obstruction (present in 25% of patients with HOCM) can lead to significant symptoms, reduction in functional capacity, angina, syncope, and sudden death. The obstruction is dynamic and is usually due to a combination of septal muscular bulging and systolic anterior motion of the anterior mitral valve leaflet (SAM)—the latter results from a Venturi effect rather than from intrinsic mitral valve disease. In addition to contributing significantly to LVOT obstruction, SAM can also lead to mitral regurgitation in the setting of HOCM.

SAM also occurs in patients post mitral valve surgical annuloplasty where an annuloplasty ring has resulted in excess longitudinal apical displacement of the anterior leaflet tip (redundant) and subsequent SAM in the absence of septal hypertrophy. LVOT obstruction secondary to SAM is also recognized to occur in patients (often elderly) with a sigmoid intraventricular septum in the absence of HOCM.

Methods of treating SAM in patients with HOCM include surgical septal myectomy and catheter based alcohol septal ablation.

Surgical septal myectomy is an open heart operation performed to relieve symptoms in patients who remain severely symptomatic despite medical therapy. It has been performed successfully for more than 25 years. Surgical septal myectomy uniformly decreases left ventricular outflow tract obstruction and improves symptoms, and in experienced centers has a surgical mortality of less than 1%, as well as 85% success rate. It involves a median sternotomy (general anesthesia, opening the chest, and cardiopulmonary bypass) and removing a portion of the interventricular septum. Surgical myectomy is focused just on the subaortic LVOT section of the septum, to increase the size of the outflow tract to reduce Venturi forces may be inadequate to abolish systolic anterior motion (SAM) of the anterior leaflet of the mitral valve. With this limited sort of resection the residual mid-septal bulge still redirects flow posteriorly and SAM still persists. It is only when the deeper portion of the septal bulge is resected that flow is redirected anteriorly away from the mitral valve, abolishing SAM. With this in mind, a modification of the Morrow myectomy termed extended myectomy, mobilization and partial excision of the papillary muscles has become the excision of choice. In selected patients with particularly large redundant mitral valves, anterior leaflet plication may be added to complete separation of the mitral valve and outflow. Complications of septal myectomy surgery include possible death, stroke, AV nodal conduction block and requirement for permanent pacemaker, arrhythmias, infection, incessant bleeding, septal perforation/defect.

Transcatheter alcohol septal ablation, introduced by Ulrich Sigwart in 1994, is a percutaneous technique that involves injection of alcohol into one or more septal branches of the left anterior descending artery. This is a technique with results similar to the surgical septal myectomy procedure but is less invasive, since it does not involve general anesthesia and opening of the chest wall, pericardium, aorta or heart (which are done in a surgical septal myomectomy with mitral valve modification). In a select population with symptoms secondary to a high outflow tract gradient, alcohol septal ablation can reduce the symptoms of HCM. In addition, older individuals and those with other medical problems, for whom surgical myectomy would pose increased procedural risk, would likely benefit from the lesser invasive septal ablation procedure. When appropriate coronary septal artery anatomy exists, alcohol septal ablation induces a controlled heart attack, in which the portion of the interventricular septum that involves the left ventricular outflow tract is infarcted and will contract into a scar. The potential complications of this procedure include death, stroke, larger extensive myocardial infarction, AV nodal conduction block with requirement for permanent pacemaker, infection, and arrhythmias.

US2008/086164 (Rowe) discloses heart implants for treatment of globular left ventricle, which is the opposite to hypertrophic cardiomyopathy with LVOT obstruction (HOCM), by implanting a device configured to elongate the left ventricle to restore a conical shape and reverse widening and rounding of the left ventricle. Such a device could potentially make LVOT obstruction worse in the context of HOCM.

US2007/0061010 (Hauser) discloses a solution for mitral annular dilation and resultant functional mitral regurgitation which occurs in left ventricular dilation (i.e. in dilated cardiomyopathy rather than hypertrophic cardiomyopathy) that involves implanting a device configured to compress the mitral valve annulus directly or indirectly to reduce mitral annular dilation. Such a device would not prevent leaflet and sub-valvular apparatus from migrating into the LVOT in systole in patients with HOCM.

US2014/0100596 (Rudman) describes methods for reducing blood volume in the left atrial appendage by implanting a volume-adding member having an impermeable membrane. Such a device would have no effect on HOCM.

It is an object of the invention to overcome at least some of the above-referenced problems.

STATEMENTS OF INVENTION

The invention provides an implantable intracardiac device for preventing systolic anterior motion of the anterior mitral valve leaflet into the left ventricular outflow tract (hereafter "device" or "anti-SAM device"). The device comprises a deflecting member configured for implantation within the left ventricle of the heart and in-situ block of systolic anterior motion of the mitral valve into the left ventricular outflow tract, and thereby improves and increases blood flow out through the left ventricular outflow tract (LVOT) into the aorta. The device is preferably configured for percutaneous delivery to the left ventricle of the heart by means of a catheter, and is typically configured to be anchored in place by means of one or more anchoring elements. In another embodiment, the device is configured for delivery during open heart surgery, for example by means of aortotomy, transatrial or transventricular surgery. The device can be employed in patients with dynamic LVOT obstruction, HOCM, or employed in patients post mitral valve surgical annuloplasty with resultant SAM or in patients having a sigmoid intraventricular septum with symptomatic outflow tract obstruction.

Thus, in a first aspect, the invention provides an implantable intracardiac device to prevent systolic anterior motion of the anterior mitral valve leaflet into the left ventricular outflow tract, the device comprising a blocking member configured for implantation within the left ventricle of the heart and in-situ blocking of systolic anterior motion of the mitral valve into the left ventricular outflow tract.

An implantable intracardiac device of the invention obviates the requirement for surgical myectomy or alcohol septal ablation in HOCM patients with SAM, avoids the creation of myocardial scar as occurs in alcohol septal ablation and thereby have a lower risk of pro-arrhythmia. In addition, the efficacy of the device can be assessed acutely in real time during implantation to ensure optimal sizing and deployment. Moreover, the radial force required of such a device is low as it only needs to overcome the Venturi effect of the left ventricular outflow tract (LVOT). Although the device is primarily designed to prevent LVOT obstruction (it may also prevent mitral regurgitation secondary to SAM). In one embodiment, the blocking member is configured for implantation within the left ventricle of the heart without compression or re-shaping of the mitral valve annulus.

Typically, the device is configured for radial expansion (ideally radial self-expansion) from a contracted orientation suitable for transluminal delivery to the left ventricle of the heart within a suitable delivery vehicle and an expanded orientation suitable for deployment within the left ventricle of the heart.

Preferably, the device comprises an anchoring element configured for anchoring the device in-situ within the left ventricle, preferably to a wall of the left ventricle. In one embodiment, the device comprises an anchoring element configured for anchoring the device to the interventricular septum. In one embodiment, an anchoring element is disposed towards the proximal end of the blocking member. In one embodiment, an anchoring element is disposed towards the distal end of the blocking member. In one embodiment, the device comprises two anchoring elements configured for anchoring the device to the interventricular septum. In one embodiment, an anchoring element is disposed towards the distal end of the blocking member and another anchoring element is disposed towards a proximal end of the blocking member.

In one embodiment, the anchoring element is disposed at a side of the blocking member and configured for engagement with a wall of the left ventricle, in one embodiment the interventricular septum (i.e. LVOT septum or left ventricular mid-septum) upon rotation of the device adjacent to the wall along an axis generally parallel to the wall of the left ventricle. In one embodiment, the anchoring means is a coil. In one embodiment, the blocking member is a generally cylindrical member having a longitudinal axis and the anchoring element is coil having an axis generally parallel to the longitudinal axis of the generally cylindrical member. Typically, the device comprises a blocking member having a proximal end and a distal end, and anchoring elements disposed at the distal end, the proximal end, or both the distal end and proximal end. In one embodiment, the device comprises a blocking member, an anchoring element, and a stem connecting the blocking member and anchoring element. This allows the device to be anchored to a wall of the left ventricle that is remote from the left ventricle outflow tract allowing the blocking member to be positioned at or adjacent to the outflow tract. In one embodiment, the anchoring element is attached to the blocking member for rotation independent of the blocking member.

Preferably, the device comprises a transition member disposed between an anchoring element and the blocking member (for example disposed on the stem). The purpose of the transition member is to provide some flexibility such that torque exerted on the blocking member is not fully transmitted to the anchoring element.

Thus, in a preferred embodiment, the invention provides an implantable intracardiac device preferably configured for radial self-expansion from a contracted orientation suitable for transluminal delivery to the left ventricle of the heart within a suitable delivery vehicle and an expanded orientation suitable for deployment within the left ventricle of the heart, the device comprising a blocking member configured for in-situ blocking of systolic anterior motion of the mitral valve into the left ventricular outflow tract, and an anchoring element configured for anchoring the device to a wall of the left ventricle, and optionally a transition member operably connecting the anchoring element and the blocking member configured to absorb torque and allow deflection of the blocking means relative to the anchoring element when in a deployed configuration.

Preferably, at least one anchoring element is provided at a distal end of the device. Alternatively, at least one anchoring element is provided at a proximal end of the device. Ideally, the device comprises at least two spaced-apart anchoring elements. Preferably, the device comprises a first anchoring element provided at a distal end of the device and a second anchoring element provided at a proximal end of the device. In this embodiment, the blocking member is disposed intermediate the proximal and distal anchoring element.

In one embodiment, the device is configured such that in-situ the anchoring element anchors the device to wall of the left ventricle, preferably the interventricular septum. Ideally, when the device comprises two anchoring elements, the device is configured such that in-situ the two anchoring elements anchor the device to the left ventricular septum. Ideally, the device comprises a proximal anchoring element configured to anchor a proximal end of the device to the left ventricular outflow tract (LVOT) septum and a distal anchoring element configured to anchor the distal end of the device to the left ventricular septum (a) intermediate the LVOT septum and the apex of the left ventricular septum or (b) at, above, or adjacent to the apex of the left ventricular septum.

In another embodiment, the device comprises a proximal anchoring element configured to anchor a proximal end of the device to the aorto-mitral continuity and a distal anchoring element configured to anchor the distal end of the device above or adjacent to the apex of the left ventricular septum.

In another embodiment, the device comprises a proximal anchoring element configured to anchor a proximal end of the device to the left ventricular septum and a distal anchoring element configured to anchor the distal end of the device to the lateral wall of the left ventricle.

Typically, each anchoring element comprises a fixing screw, ideally an active fixation anchoring screw. In another embodiment, the anchoring element comprises a barbed member. In another embodiment, the anchoring element comprises a transmyocardial stud with a link to the other side of the ventricular myocardium (through to either the right side of interventricular septum or through to the epicardium of the left ventricular free wall).

Preferably, the blocking member comprises a cylindrical member, having a hollow lumen. Examples include helical elements (e.g. coils) and cylindrical cages (e.g. formed from a braid or mesh). In one embodiment, an anchoring means is disposed on a periphery of the cylindrical member. In one embodiment anchoring means are disposed on a periphery of the cylindrical member, at each end of the cylindrical member. In one embodiment, the anchoring means are aligned along a longitudinal axis of the cylindrical member. In one embodiment, the blocking member comprises a helical element, for example a coil. Typically, the helical element comprises a coiled element such as a coiled wire or coiled ribbon. Preferably, the helical element has a length of 4-6 cm. Typically, the helical element has a distal end having a diameter of 2-3 cm and a proximal end having a diameter of 0.5-1.5 cm.

Preferably, the helical element comprises an inwardly tapering section disposed towards a distal end thereof. Preferably, the helical element comprises a non-tapering proximal portion and an inwardly tapering distal portion. Preferably, the non-tapering proximal portion has a diameter of 2-3 cm and a length of 3-4 cm. Typically, the inwardly tapering distal portion has a length of 1-2 cm. Suitably the diameter of the helical element decreases from 2-3 cm to 0.5 to 1.5 cm.

Preferably, the anchoring element is configured for engaging the wall of the left ventricle in a direction substantially parallel to a longitudinal axis of the blocking member. This embodiment is suitable for when the device is configured for anchoring to the left ventricular septum.

Alternatively, the anchoring element is configured for engaging the wall of the left ventricle in a direction substantially perpendicular to a longitudinal axis of the device.

In one embodiment in which the device comprises distal and proximal anchoring elements, the distal and proximal anchoring elements are both configured for engaging the wall of the left ventricle in a direction substantially perpendicular to a longitudinal axis of the device. In this embodiment, the blocking member is preferably a helical element.

In a preferred embodiment of the invention, the device comprises a helical blocking member having a distal end and a proximal end, an anchoring element disposed on the proximal end configured for anchoring the distal end to the left ventricular outflow tract (LVOT) septum, an anchoring element disposed on the distal end configured for anchoring the distal end to the left ventricular mid septum (i.e. intermediate the LVOT septum and the apex of the left ventricular septum), and a transition member connecting the distal anchoring element and the blocking means configured to allow deflection of the blocking means when in a deployed configuration.

In another embodiment of the invention, the device comprises a helical blocking member having a distal end and a proximal end, an anchoring element disposed on the distal end configured for anchoring the distal end to the apex of the left ventricular septum, and a transition member connecting the distal anchoring element and the helical blocking means configured to allow deflection of the blocking means when in a deployed configuration.

In these embodiments, the blocking means preferably comprises a helical member. Alternatively, the blocking means may comprise another structure configured to prevent, in use, systolic anterior motion of the mitral valve. Examples of alternative blocking means includes a cage, an arched band, a cylindrical band, a straight or curved arm, or a basket. Examples of alternative blocking means are provided in the figures below.

For example, the blocking member may comprise a cage configured to fit within the left ventricle at least partly within the LVOT. The cage may comprise radial struts, longitudinal struts, or both. The cage typically comprises a hollow lumen to allow for passage of blood. The blocking member may also comprise an arched band, formed of a ribbon material or a plurality of struts, and typically configured to be anchored at each end to the left ventricular septum. The blocking member may also comprise a curved arm, and typically configured to be anchored at each end to the left ventricular septum or alternatively anchored on the posterior and anterior left ventricular wall to run as a restraining band perpendicular to the anterior mitral leaflet and chordae. The blocking member may also comprises a substantially straight arm, and typically configured to be anchored between the left ventricular septum and lateral wall of the left ventricle (i.e. laterally across the left ventricle). The blocking member may also comprise a substantially straight arm, and typically configured to be anchored between the apex of the left ventricular septum and the aorta mitral continuity (i.e. substantially vertically across the left ventricle).

In one embodiment, the device comprises a fixing plate configured to engage with the anchoring element. In this embodiment, the fixing plate is mounted externally of the heart and configured to engage with the anchoring element across the supporting wall or septum.

The transition member typically operably connects a distal anchoring element and the blocking member. It generally comprises a flexible region that allows some "play" between the anchoring means and the bearing means. The anchoring element may comprise a helical member or a non-helical member. The transition member may comprise a straight member or a curved member. Typically, the transition member is substantially straight—an example of such an embodiment is a device configured to allow for the anchoring element to engage the apex of the left ventricular septum. Alternatively, the transition member is curved such that when in a deployed orientation the anchoring element engages the left ventricular septum. In one embodiment, the transition member comprises a helical part. Preferably, when the blocking member comprises a helical member, the pitch of the helical part of the transition member is different to the pitch of the helical member.

In one embodiment of the invention, the transition member is configured to allow resilient deformation of the transition member. Preferably, at least a part of the transition member is crimped.

The invention also provides a delivery catheter for percutaneous delivery of an implantable intracardiac device to the left ventricle of the heart and anchoring the implantable intracardiac device in-situ within the left ventricle of the heart. In one embodiment, the delivery device is configured for delivering an implantable intracardiac device comprising a radially expandable blocking body and distal and proximal anchoring coils. In one embodiment, the delivery catheter comprises a proximal end having a control module and a distal end having an outer sheath and an inner sheath, in which the outer sheath is operably connected to the control module and configured for axial movement relative to the inner sheath upon actuation of the control module, in which the inner sheath is configured to receive the radially expandable body and comprises a longitudinal slot configured to allows the anchoring coils embrace the inner sheath while the radially expandable blocking body is disposed within the inner sheath. An embodiment according to this embodiment of the invention is described in FIGS. 24 to 29.

In one embodiment, the longitudinal slot is open at a distal end of the sheath. In one embodiment, the sheath has a length that is substantially equivalent to the length of the radially blocking body in a contracted configuration.

The invention also provides a delivery catheter for percutaneous delivery of an implantable intracardiac device to the left ventricle of the heart and anchoring the implantable intracardiac device in-situ within the left ventricle of the heart, in which the implantable intracardiac device of the invention comprises a radially expandable blocking body and distal and proximal anchoring coils, and in which the delivery catheter comprises a proximal end having a control module and a distal end having an outer sheath, an inner sheath, and a mid sheath disposed between the inner and outer sheaths, in which an end of the mid sheath is configured to engage the distal anchoring coil and an end of the inner sheath is configured to engage the proximal anchoring coil, and in which the outer and mid sheaths are operably connected to the control module and configured for independent axial movement upon actuation of the control module, and in which the inner sheath is operably connected to the control module and configured for rotational movement. An embodiment according to this embodiment of the invention is described in FIGS. 24 to 29.

In one embodiment, the distal anchoring coils are configured to embrace the inner sheath. In one embodiment, the anchoring coils comprise a diametrical head and an end of the inner and outer sheath comprise complimentary fittings for engagement of the diametrical head, preferably in a snap-fit manner.

The invention also relates to a method of deploying a device of the invention comprising the steps of placing the device in a contracted orientation within a deflectable sheath forming part of an elongated catheter member, advancing the catheter member including the device of the invention within the sheath along a blood vessel into the left ventricle, optionally anchoring the anchoring element to a wall of the left ventricle, and withdrawing the sheath to deploy the device in which deployed configuration the blocking member of the device bears against the anterior mitral valve leaflet preventing systolic anterior motion of the mitral valve into the left ventricular outflow tract.

The invention also relates to a method of preventing or inhibiting systolic anterior motion of the anterior mitral valve leaflet in a mammal, the method comprising a step of inserting and positioning an implantable intracardiac blocking device within the left ventricle of the heart of the mammal whereby the device when inserted blocks systolic anterior motion of the anterior mitral valve leaflet into the left ventricular outflow tract.

The invention also relates to a method of preventing or inhibiting left ventricular outflow tract obstruction in a mammal, the method comprising a step of inserting and positioning an implantable intracardiac blocking device within the left ventricle of the heart of the mammal whereby the device when inserted blocks systolic anterior motion of the anterior mitral valve leaflet into the left ventricular outflow tract thereby preventing or inhibiting left ventricular outflow tract obstruction.

The invention also relates to a method of preventing or inhibiting hypertrophic obstructive cardiomyopathy (HOCM) in a mammal, the method comprising a step of inserting and positioning an implantable intracardiac blocking device within the left ventricle of the heart of the mammal whereby the device when inserted blocks systolic anterior motion of the anterior mitral valve leaflet into the left ventricular outflow tract thereby preventing or inhibiting hypertrophic obstructive cardiomyopathy (HOCM).

The invention also relates to a method of treating a patient with left ventricular outflow tract obstruction in a patient having had post mitral valve surgical annuloplasty, the method comprising a step of inserting and positioning an implantable intracardiac blocking device within the left ventricle of the heart of the patient subsequent to post mitral valve surgical annuloplasty whereby the device when inserted blocks systolic anterior motion of the anterior mitral valve leaflet into the left ventricular outflow tract thereby preventing or inhibiting left ventricular outflow tract obstruction.

The invention also relates to a method of treating a patient with a sigmoid intraventricular septum and symptomatic left ventricular outflow tract obstruction, the method comprising a step of inserting and positioning an implantable intracardiac blocking device within the left ventricle of the heart of the patient subsequent to post mitral valve surgical annuloplasty whereby the device when inserted blocks systolic anterior motion of the anterior mitral valve leaflet into the left ventricular outflow tract thereby preventing or inhibiting left ventricular outflow tract obstruction thereby treating a patient with a sigmoid intraventricular septum and symptomatic left ventricular outflow tract obstruction.

In the above methods, the blocking member is preferably anchored in position in the left ventricle. Typically, the blocking device comprises one or more anchoring elements configured to anchor the device in position. In one embodiment of the methods of the invention, the implantable intracardiac device is an implantable intracardiac device of the invention.

Typically, the blocking device is inserted into the left ventricle of the heart percutaneously and transluminally. Preferably, the blocking device is inserted into the left ventricle via the right femoral artery and retrogradely across the aortic valve. Alternatively, the blocking device is inserted into the left ventricle via a right femoral vein transseptal approach.

Definitions:

"Implantable intracardiac device" means a device that is dimensioned for implantation in the left ventricle of the heart and which is formed of materials that are biocompatible, i.e. do not normally promote an immune response in the host and or cause trauma, inflammation or scarring. Examples of such materials include gold, titanium, cobalt-chromium alloy, tantalum alloy, nitinol, and several polymers.

"Configured for expansion" means that the device is capable of expanding from a contracted orientation to a deployment orientation. Typically, the device is configured for self-expansion—this may be achieved due to elasticity or shaped-memory of the materials being employed. Suitably, the device is configured for radial expansion upon deployment (for example, when the bearing member is a helical member).

"Delivery vehicle" means a device suitable for delivery of a device of the invention through the lumen of a blood vessel into the left ventricle of the heart. Typically, the delivery device is a catheter. Examples of suitable catheters for transluminal delivery of intracoronary devices are known in the art, for example TAVI devices.

"Blocking member" means a member that when implanted and positioned within the left ventricle prevents systolic anterior motion of the anterior mitral valve leaflet, but does not prevent or unduly inhibit blood flow through the left ventricular outflow tract (LVOT). Generally, the device is positioned such that at least a part of the blocking member is disposed within the LVOT. Typically, the blocking member is elongated (i.e. it has a longitudinal aspect that is generally longer than a lateral aspect). Examples of blocking members within the meaning of the present invention are described below and illustrated in the accompanying figures. The elongated member is typically anchored at one end, either the distal end, the proximal end, or both. The member may be formed from various biocompatible materials, for example metal wire or ribbon or an elastic material (for example a band) and may be straight, curved, arched, and helical. The blocking means may take a number of different forms, for example a helical member (i.e. coil), a cage, a balloon, an arched member, a straight or curved ribbon-like member, and is typically anchored in position by means of an anchoring means disposed at either or both ends of the device.

"Anchoring element" means an element configured for engaging a wall or septum of the left ventricle of the heart. In one embodiment the anchoring means is an active fixation screw, for example a helical coil, similar (but preferably larger) to the active fixation screws employed for anchoring pacemaker leads. In another embodiment, the anchoring means is a barbed tine. In one embodiment, the anchoring element is a helical coil disposed on a side of the blocking member and configured to engage a wall of the left ventricle upon rotation of the blocking member.

"Active fixation anchoring screw" means a fixation screw or element adapted for anchoring to a wall of the heart. They are commonly used to anchor pacemaker leads to the wall of the heart. Examples of such active fixation screws are described in WO2009070074.

"Wall of the left ventricle" means a wall or septum of the left ventricle. Examples include the left ventricular septum, LVOT septum, apex of the left ventricular septum, aortomitral valve continuity, and lateral wall of the left ventricle.

"Transition member" means a part of the device connecting the anchoring means and the blocking member that is sufficiently flexible to allow a degree of "play" between the anchoring means and the blocking member such that torque exerted on the blocking member is not fully transmitted to the anchoring means. The transition member may comprise a straight or curved wire that is resiliently deformable (i.e. bendable), or it may comprise a section of crimped wire, or it may comprise a helical section of wire.

"Left ventricular outflow tract septum" means the upper part of the septum adjacent the left ventricular outflow tract below the aortic annulus.

"Left ventricular mid septum" means the part of the left ventricular septum intermediate the LVOT septum and the apex of the left ventricular septum.

"Helical member" means a member formed of a plurality of helical coils, generally at least 3, 4 or 5 coils. Preferably, the helical member is inwardly tapering towards a distal end of the device (i.e. tapering towards the lower end of the left ventricle). Typically, the helical member has a length of about 4-6 cm, ideally about 5 cm. Typically, the helical member has a radial diameter of 1.5 to 3 cm, preferably about 2-2.5 cm.

"Percutaneously" means delivered through the skin without requirement for surgical incision and "Translumninally" means through a blood vessel.

BRIEF DESCRIPTION OF THE FIGURES

The invention will be more clearly understood from the following description of some embodiments thereof given by way of example only in which:

FIGS. 4 and 5 are perspective views of devices according to alternative embodiments of the invention;

FIG. 11 is a sectional illustration of a device according to an alternative embodiment of the invention in-situ within the left ventricle of the heart;

FIG. 12 is a sectional illustration of a device according to an alternative embodiment of the invention in-situ within the left ventricle of the heart;

FIG. 17A is a sectional view of a delivery device of the invention configured for delivering an implantable intracardiac device of FIGS. 15 and 16 and showing the device loaded into the delivery device.

FIG. 17B is a sectional view of the delivery device of FIG. 17A showing the outer sheath retracted exposing the distal anchoring element.

FIG. 17C is a sectional view of the delivery device of FIG. 17A showing the mid sheath retracted exposing the proximal anchoring element.

FIG. 17D is a detailed view of the engagement between the distal anchoring element and a distal end of the mid sheath.

FIG. 23 is a partly sectional view of the delivery device of FIG. 17 showing rotation of the inner sheath to anchor the proximal anchoring element in adjacent tissue.

FIG. 24A is a front elevational partially perspective view of an implantable intracardiac device according to an alternative embodiment of the invention.

FIG. 24B is a detailed view of the device of FIG. 24A showing the distal anchoring element attached to a strut of the device.

FIG. 27 is a partly sectional view of the delivery device of FIG. 26 showing the outer sheath fully retracted and the distal and proximal anchoring elements exposed.

FIG. 28 is a partly sectional view of the delivery device of FIG. 26 showing rotation of the delivery device to allow the distal and proximal anchoring element embed themselves in adjacent tissue.

FIG. 29 is a partly sectional view of the delivery device of FIG. 26 showing the mid sheath partially retracted and the implantable intracardiac device partially exposed.

FIG. 30A is a front elevational view, 30B is a side elevational view, and 30C is a top elevation view of an implantable intracardiac device according to an alternative embodiment of the invention.

FIG. 31A is a front elevational view and 31B is a side elevational view of the implantable intracardiac device of FIG. 30.

FIG. 31C is a detailed view of a distal end of the device of FIG. 30.

FIG. 36A is a front elevational view and 36B is a side elevational view of an implantable intracardiac device according to an alternative embodiment of the invention.

FIG. 36C is a detailed view of a distal end of the device of FIG. 36A.

FIG. 37A is a front elevational view and 37B is a side elevational view of an implantable intracardiac device according to an alternative embodiment of the invention.

FIG. 37C is a detailed view of a distal end of the device of FIG. 37A.

FIG. 39A is a front elevational view, 39B is a side elevational view, and 39C is a top elevation view of an implantable intracardiac device according to an alternative embodiment of the invention.

DETAILED DESCRIPTION OF THE INVENTION

Figure 1A:
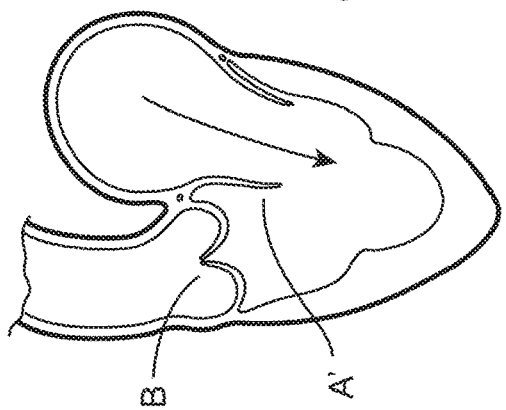
FIGS. 1A-1D are illustrations showing the problem of SAM (systolic anterior motion) of the mitral valve.
Figure 1B:
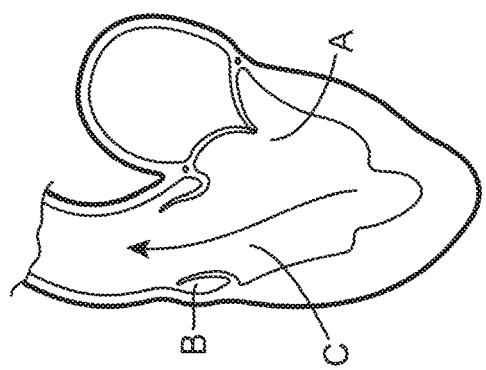
Figure 1C:
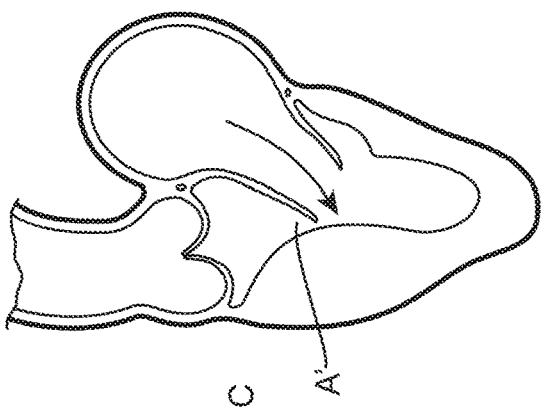
Figure 1D:
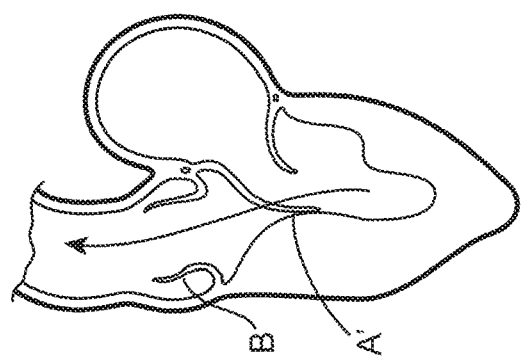

Referring initially the FIGS. 1A to 1D, the problem of systolic anterior motion of the mitral valve is illustrated. FIGS. 1A and 1B show opening and closing of the mitral valve A in the left side of a heart of a normal patient. As illustrated in FIG. 1A, when the mitral valve is open, the anterior leaflet A' of the mitral valve is clear of the left ventricular outflow tract C during systole, and does not obstruct outflow of blood through the aortic valve B. FIGS. 1C and 1D illustrate the opening and closing of the mitral valve in a HOCM patient with SAM. As indicated in FIG. 1D, during systole part of the anterior leaflet A' of the mitral valve is regurgitated into the left ventricular outflow tract (LVOT), causing an obstruction of blood flow through the outflow tract.

The method and device of the invention addresses this problem by inserting and positioning a blocking device into the left ventricle, such that the blocking device when in-situ blocks systolic anterior motion of the anterior mitral valve leaflet into the left ventricular outflow tract.

Figure 2:
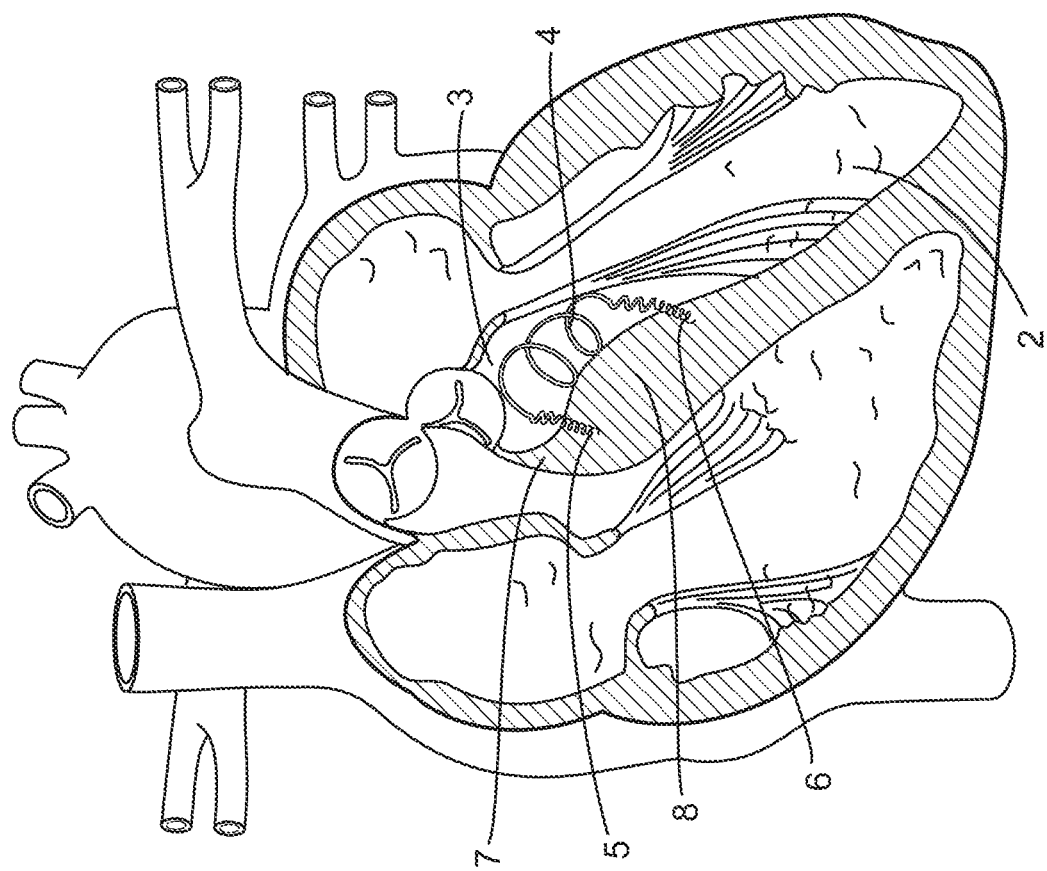
FIG. 2 is a sectional illustration of a human heart showing a device of one embodiment of the invention in-situ within the left ventricle of the heart.

Referring to FIG. 2, there is illustrated a human heart having an implantable intracardiac device according to one embodiment of the invention (indicated generally by the reference numeral 1 implanted into the left ventricle 2 adjacent to the LVOT 3. The device 1 comprises a helical blocking member 4 having a proximal active fixation screw 5 anchored into the LVOT septum 7 and a distal active fixation screw 6 anchored into the left ventricular mid septum 8. The device 1, shown in more detail in FIG. 3, also includes two transition members, in this case crimped wire zones 9 and 10, formed intermediate the proximal and distal ends of the helical member 4 and the fixation screws 5, 6. The purpose of the transition members is to absorb movement of the helical member during beating of the heart. The device is formed of NITINOL.

Referring to FIGS. 4 and 5, there are illustrated two devices 10 according to alternative embodiments of the invention in which parts identified with reference to the previous embodiments are assigned the same reference numerals. The device 10 comprises a helical member 4 having a proximal end 11, a distal end 12, a transition zone 13, and a distal fixation screw 14. The helical member 4 is approximately 4 cm in length, and has a non-tapering proximal portion 15 of diameter 2 cm and an inwardly tapering distal portion 16 having a diameter of 2 cm to 1.5 cm. The device 10 of FIG. 4 has a straight transition zone 13 formed at an oblique angle to the longitudinal axis of the device, whereas the device 10 of FIG. 5 has a straight transition zone 13 that is parallel to the longitudinal axis of the device. These embodiments of the device are designed to attach to the heart at a single point, for example the apex of the left ventricular septum.

Figure 6:
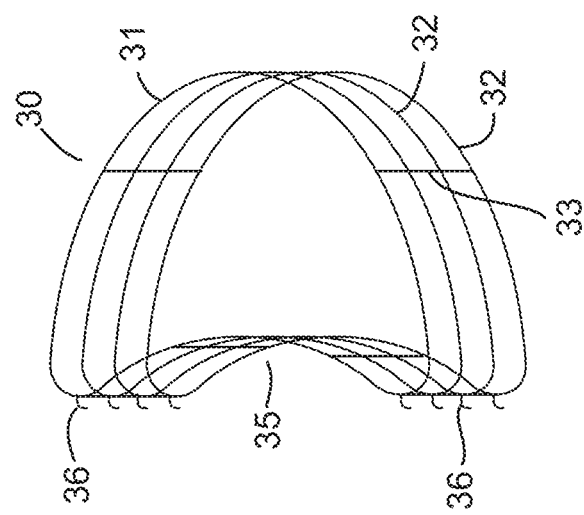
FIG. 6 is a perspective view of one embodiment of the device of the invention.

Referring to FIG. 6, there is illustrated a device according to a further embodiment of the invention, indicated generally by the reference numeral 30, and comprising a blocking member formed by an band 31 of four Nitinol wires 32 and reinforcing struts 33. The band 31 is generally semi-circular in shape and has a curved base 35 which is dimensioned to conform to the LVOT septum. The device 30 includes eight barbs 36 configured to anchor the device in-situ against the LVOT septum.

Figure 3:
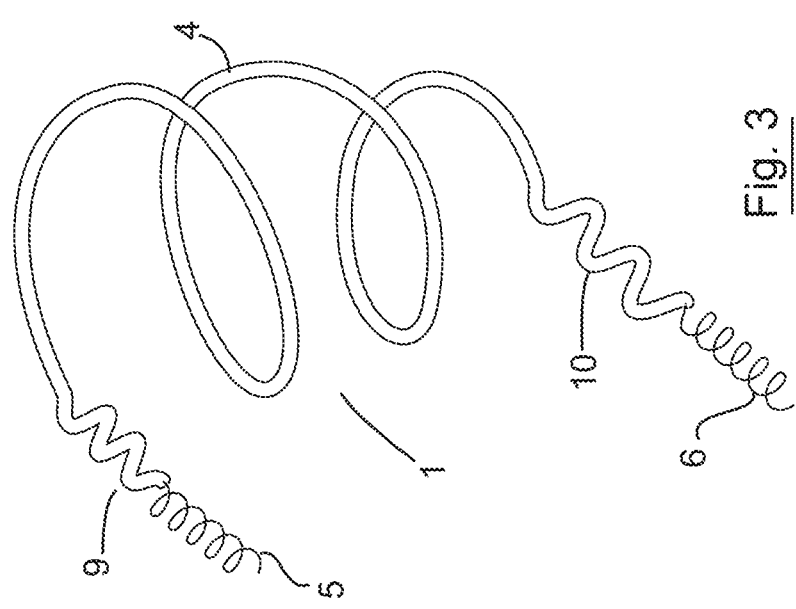
FIG. 3 is a more detailed view of the in-situ device shown in FIG. 2.
Figure 7:
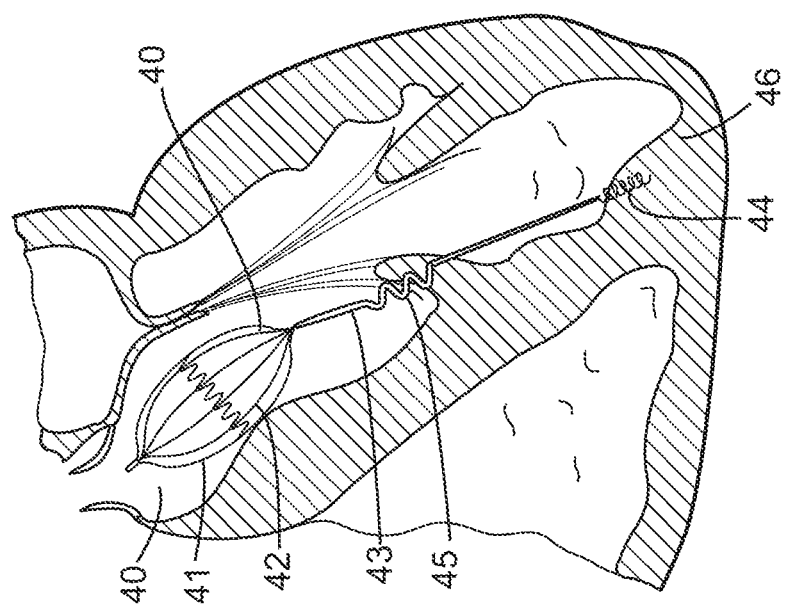
FIG. 7 is a sectional illustration of a device according to an alternative embodiment of the invention in-situ within the left ventricle of the heart.

Referring to FIG. 7, there is provided a further illustration of the device of FIG. 3 in-situ within the left ventricle of the heart, and anchored between the LVOT 7 septum and the left ventricular mid-septum 8.

Figure 8:
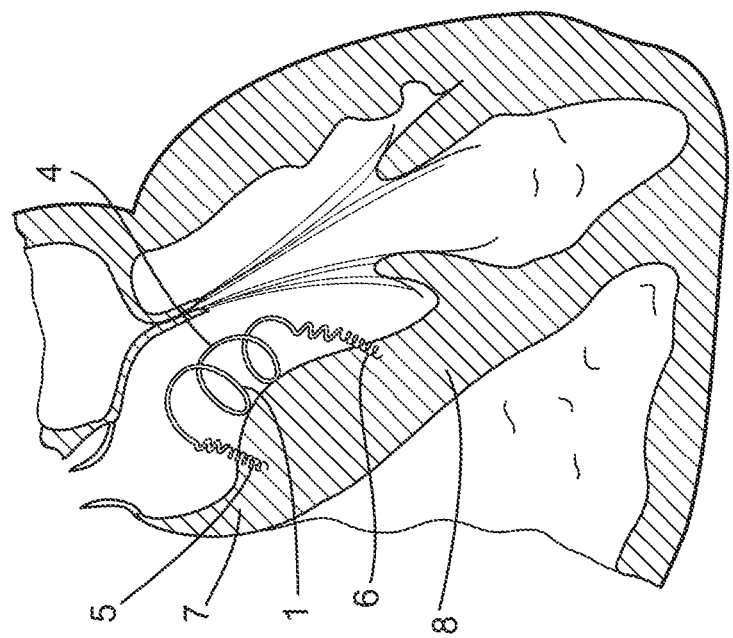
FIG. 8 is a sectional illustration of a device according to an alternative embodiment of the invention in-situ within the left ventricle of the heart.

Referring to FIG. 8, there is illustrated a device according to a further embodiment of the invention, indicated generally by the reference numeral 40, shown anchored in-situ within the left ventricle of the heart. In this embodiment, the blocking member 4 is a cage formed from a plurality of longitudinal struts 41 and one radial strut 42. The device comprises an elongated arm 43 formed of wire, a fixation screw 44 disposed at a distal end of the arm 43, and a transition zone 45 comprising a crimped section of the wire arm 43. The device is anchored into the apex 46 of the left ventricular septum.

Figure 9:
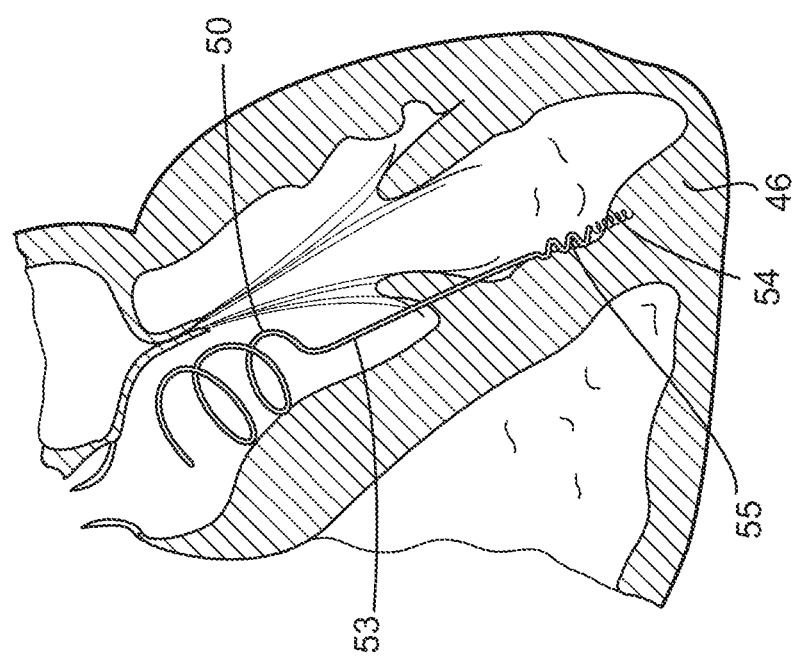
FIG. 9 is a sectional illustration of a device according to an alternative embodiment of the invention in-situ within the left ventricle of the heart.

Referring to FIG. 9, there is illustrated a device according to a further embodiment of the invention, indicated generally by the reference numeral 50, shown anchored in-situ within the left ventricle of the heart. In this embodiment, the blocking member 4 is a helical member. The device comprises an elongated arm 53 formed of wire, a fixation screw 54 disposed at a distal end of the arm 53, and a transition zone 55 comprising a crimped section of the wire arm 53. The device is anchored above the apex 46 of the left ventricular septum.

Figure 10:
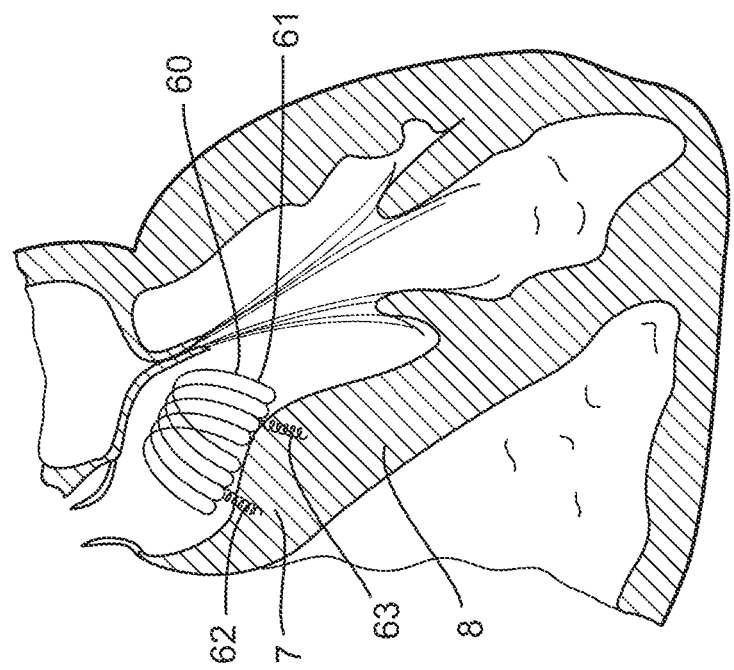
FIG. 10 is a sectional illustration of a device according to an alternative embodiment of the invention in-situ within the left ventricle of the heart.

Referring to FIG. 10, there is illustrated a device according to a further embodiment of the invention, indicated generally by the reference numeral 60, shown anchored in-situ within the left ventricle of the heart. In this embodiment, the blocking member 4 is curved band formed of Nitinol wires 61 and having a proximal end bearing a fixation screw 62 and a distal end bearing a second fixation screw 63. The screw 62 is anchored into the LVOT septum 7 and the fixation screw is anchored into the left ventricular mid-septum 8.

Referring to FIG. 11, there is illustrated a device according to a further embodiment of the invention, indicated generally by the reference numeral 70, shown anchored in-situ across the left ventricle of the heart. In this embodiment, the device comprises an elongated arm 73 formed of wire, a fixation screw 74 disposed at a distal end of the arm 73, and a disc-shaped blocking member 75 disposed on a proximal end of the arm 73. The device is anchored into the lateral wall of the left ventricle 77.

Referring to FIG. 12, there is illustrated a device according to a further embodiment of the invention, indicated generally by the reference numeral 80, shown anchored in-situ within the left ventricle of the heart. In this embodiment, the blocking member 4 is an arm formed from two substantially rigid Nitinol wires 81. The device comprises an elongated arm 83 formed of Nitinol wire, and a fixation screw 84 disposed at a distal end of the arm 83. The device is anchored into the apex 46 of the left ventricular septum.

Figure 13:
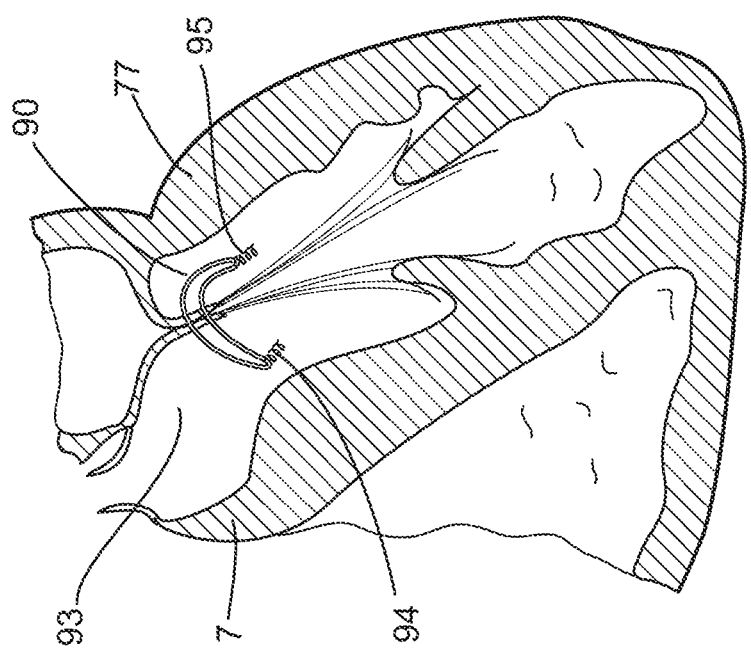
FIG. 13 is a sectional illustration of a device according to an alternative embodiment of the invention in-situ within the left ventricle of the heart.

Referring to FIG. 13, there is illustrated a device according to a further embodiment of the invention, indicated generally by the reference numeral 90, shown anchored in-situ across the left ventricle of the heart from the anterior wall to the posterior wall. In this embodiment, the device comprises an elongated arm 93 formed of Nitinol wire, a middle section of which acts as the blocking member, and fixation screws 94, 95 disposed at each end of the arm 93. The device is anchored between the anterior and posterior walls of the left ventricle.

Figure 14:
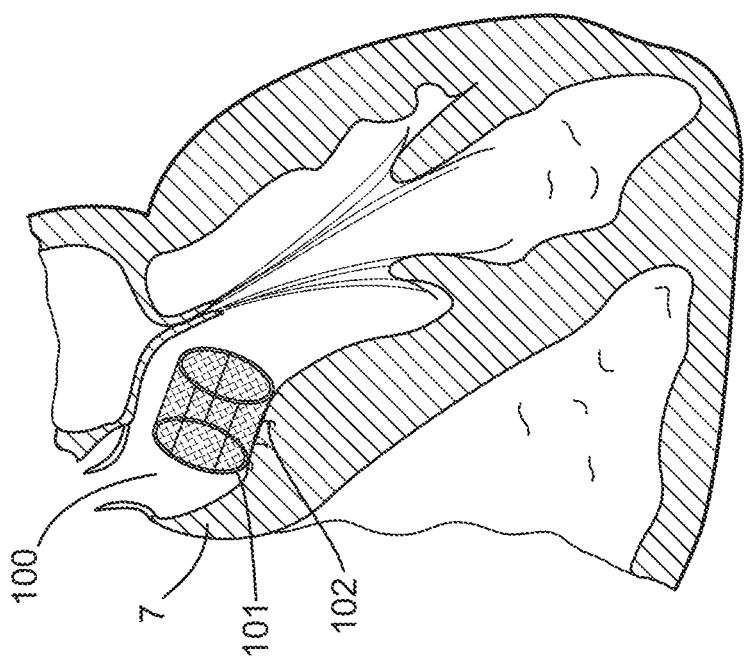
FIG. 14 is a sectional illustration of a device according to an alternative embodiment of the invention in-situ within the left ventricle of the heart.

Referring to FIG. 14, there is illustrated a device according to a further embodiment of the invention, indicated generally by the reference numeral 100, shown anchored in-situ within the left ventricle of the heart. In this embodiment, the blocking member 4 is a cylindrical cage formed of braided Nitinol wires 101 and a series of anchoring barbs 102 disposed across one end of the cage that are anchored into the left ventricular septum 7.

Figure 15A:
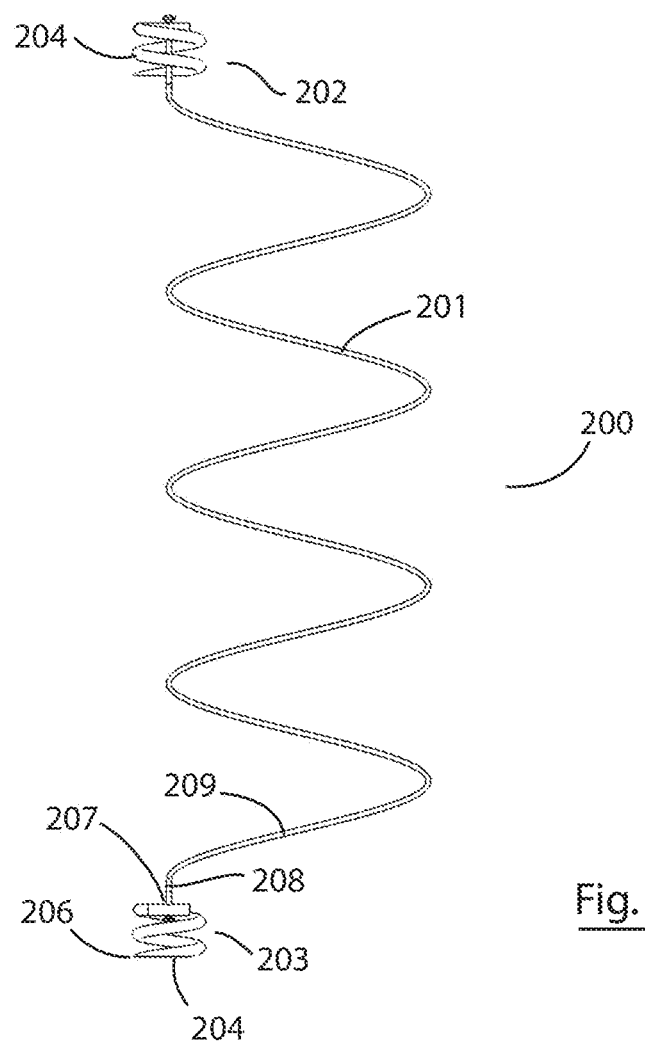
FIG. 15A is an elevational view.
Figure 15B:
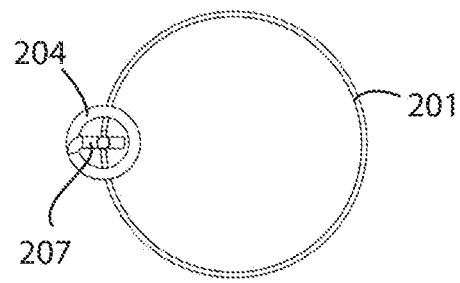
FIG. 15B is a top plan view, of an implantable intracardiac device according to an alternative embodiment of the invention.
Figure 16A:
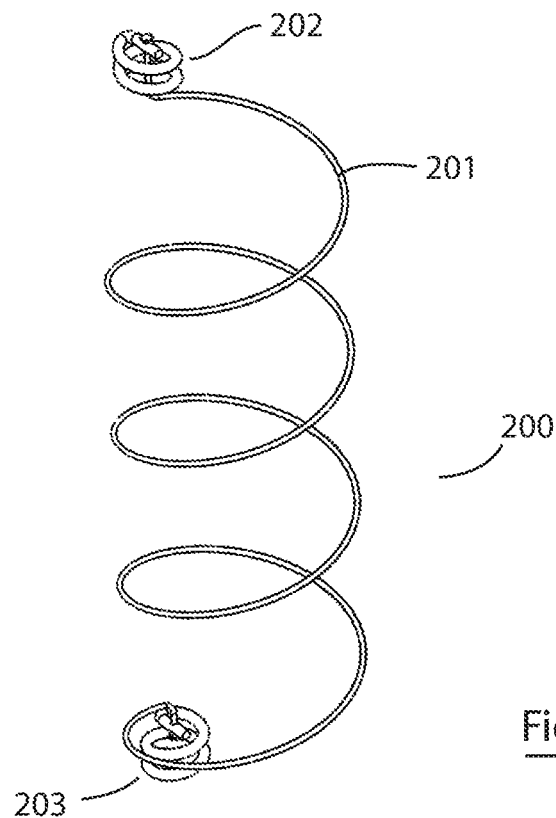
FIG. 16A is a perspective view of the implantable intracardiac device of FIG. 15
Figure 16B:
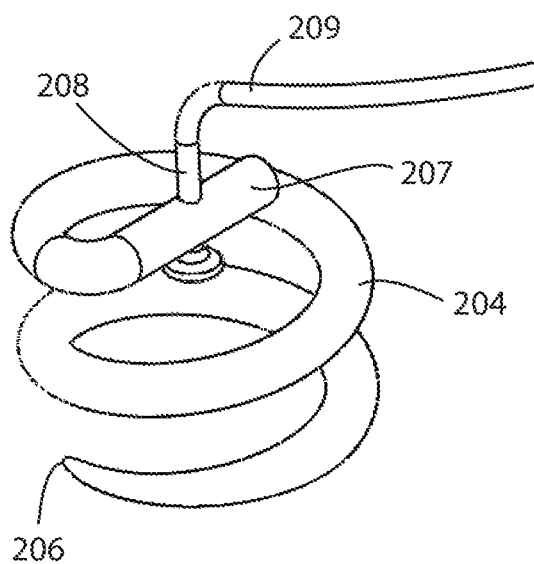
FIG. 16B is detailed view of the distal anchoring element of FIG. 15.

Referring to FIGS. 15A and 15B, there is illustrated a device according to a further embodiment of the invention, indicated generally by the reference numeral 200 and comprising a blocking member formed of a helical coil 201 having a proximal anchoring element 202 and distal anchoring element 203 formed at the end of the coil 201 and longitudinally aligned along a side of the coil to enable engagement with tissue adjacent the coil 201. In more detail and referring to FIG. 16B, the distal anchoring element 202 comprises a corkscrew anchor 204 with a piercing tip 206 at a distal end and a diametrical head 207 at a proximal end having a through-hole for receipt of a stem 208 formed on a distal end 209 of the coil 201, allowing the corkscrew anchor 204 rotate freely with respect to the coil 201. Referring to FIG. 16A the proximal anchoring element has a similar construction to the distal anchoring element with the exception that the diametrical head 207 is disposed at the proximal end, and the piercing tip 206 is disposed at the distal end, of the corkscrew anchor 204, and a stem 210 formed on a proximal end of the coil 201 extends up through the corkscrew anchor 204.

Figure 18:
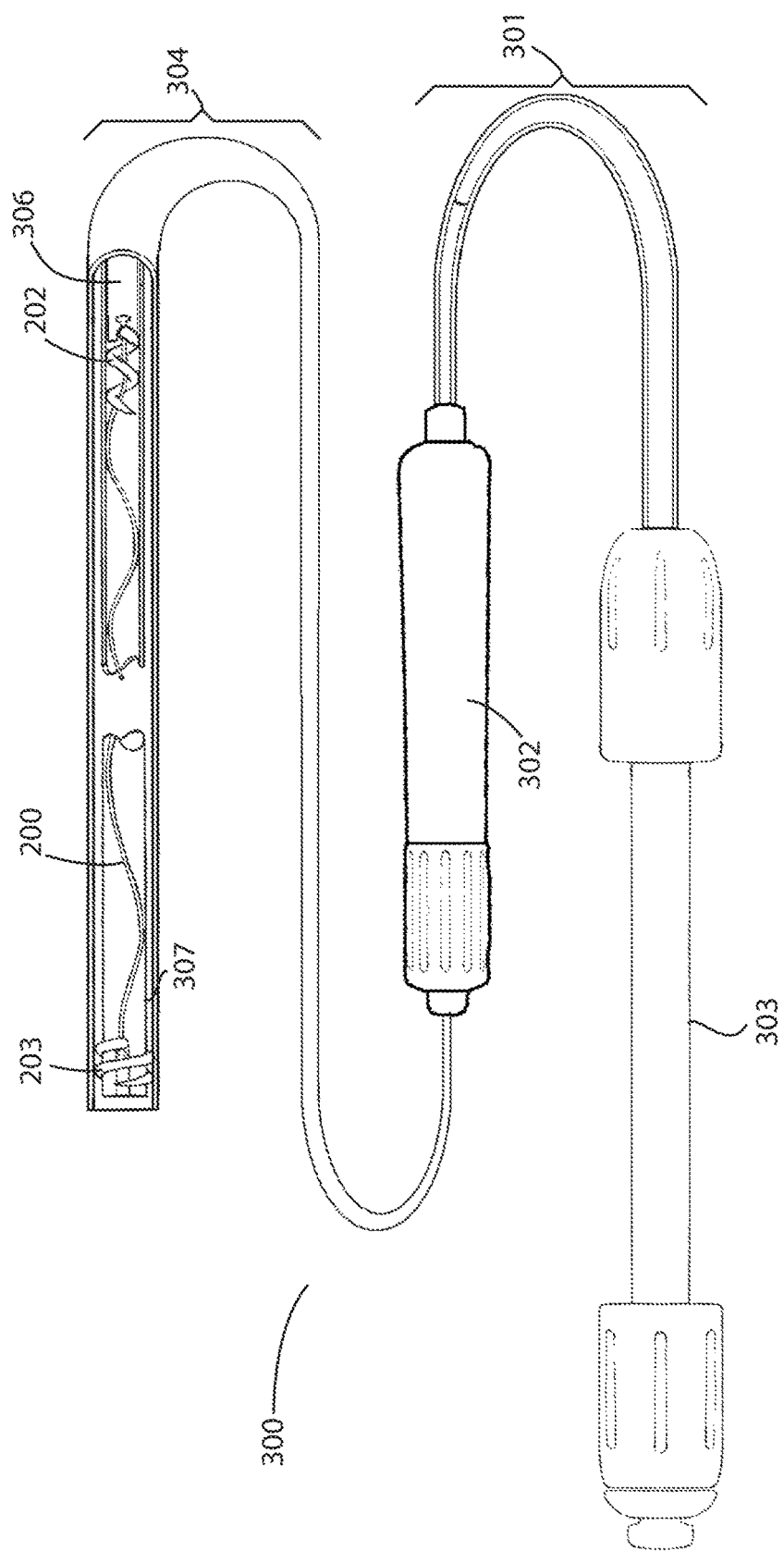
FIG. 18 is a partly sectional view of the delivery device of FIG. 17 showing the implantable intracardiac device in-situ within the device during delivery.

Referring to FIGS. 17-23, a delivery device for the implantable intracardiac device of FIGS. 15 and 16, and it use in delivering the device into the left ventricle of the heart, is illustrated. Referring initially to FIG. 18, the delivery device comprises a catheter 300 having a proximal end 301 with control handle elements 302, 303, and a distal end 304 configured to receive the device 200. In more detail, and referring to FIGS. 17A to 17D, the distal end 304 of the catheter comprises an outer sheath 305, an inner sheath 306, and a mid sheath 307 disposed between the outer and inner sheaths. The outer sheath is movable from an extended position shown in FIG. 17A to a withdrawn position shown in FIG. 17B by actuation of the handle element 302, exposing the distal corkscrew anchor 204. The mid sheath is movable from an extended position shown in FIG. 17B to a withdrawn position shown in FIG. 17C by actuation of the handle 302, exposing the device 200 including the proximal corkscrew anchor 204. The inner sheath 306 is rotatable in response to rotation of the control handle element 303.

Referring to FIG. 17D, a distal end of the inner sheath 306 includes a diametrical slot 310 configured to receive the diametrical head 207 of the proximal corkscrew anchor 204 in a snap-fit manner. This arrangement allows the user remotely rotate the anchor 204 into engagement with adjacent tissue by means of rotation of the control handle element 303 and consequent rotation of the inner sheath 306. Once the anchor 204 is engaged with tissue, retraction of the catheter 300 releases the anchor from the inner sheath 306. The distal end of the outer sheath 305 includes a similar diametrical slot 310 for engagement with the diametrical head 207 of the distal corkscrew anchor 204.

Figure 19:
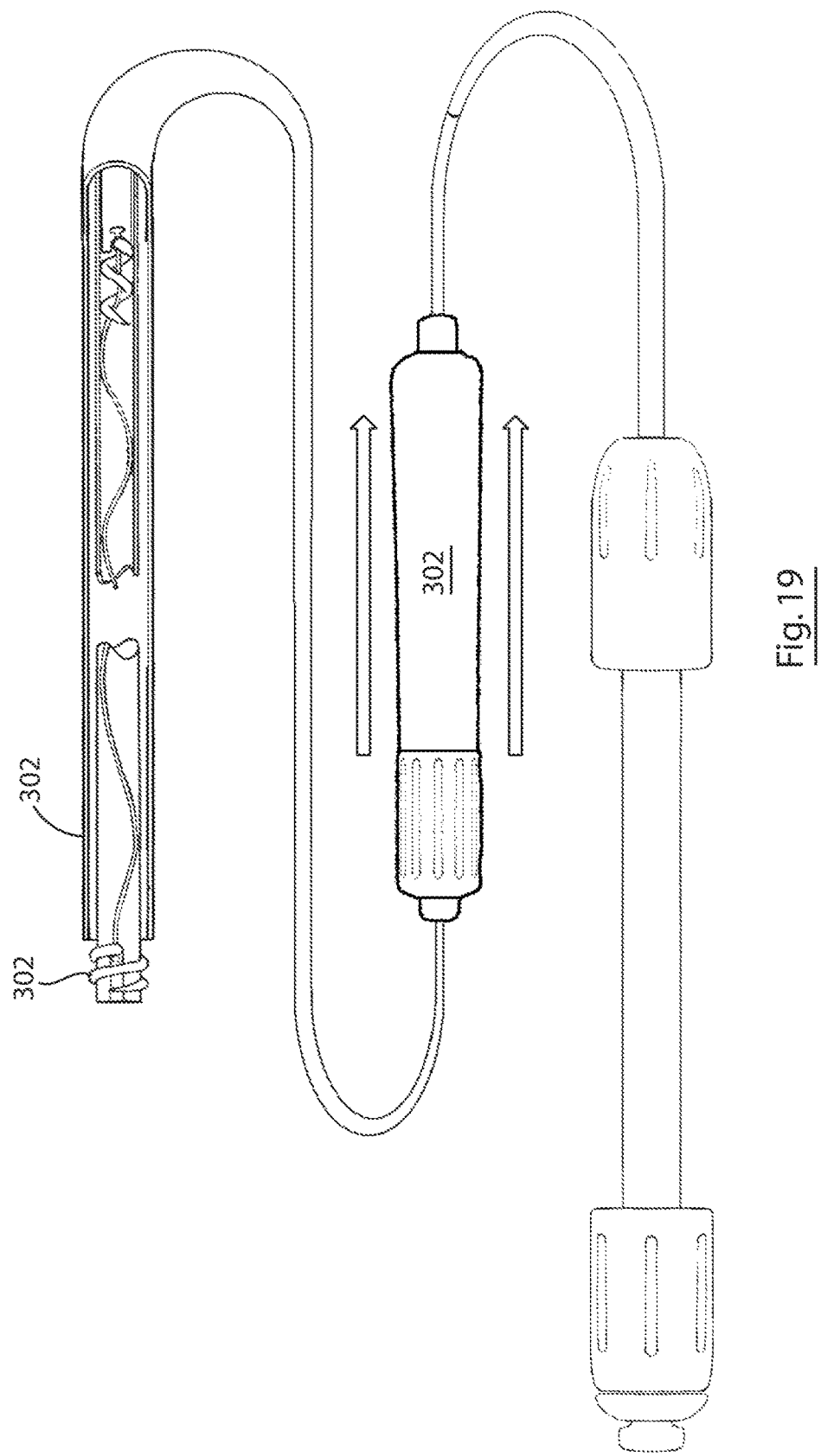
FIG. 19 is a partly sectional view of the delivery device of FIG. 17 showing the outer sheath partly retracted.
Figure 20:
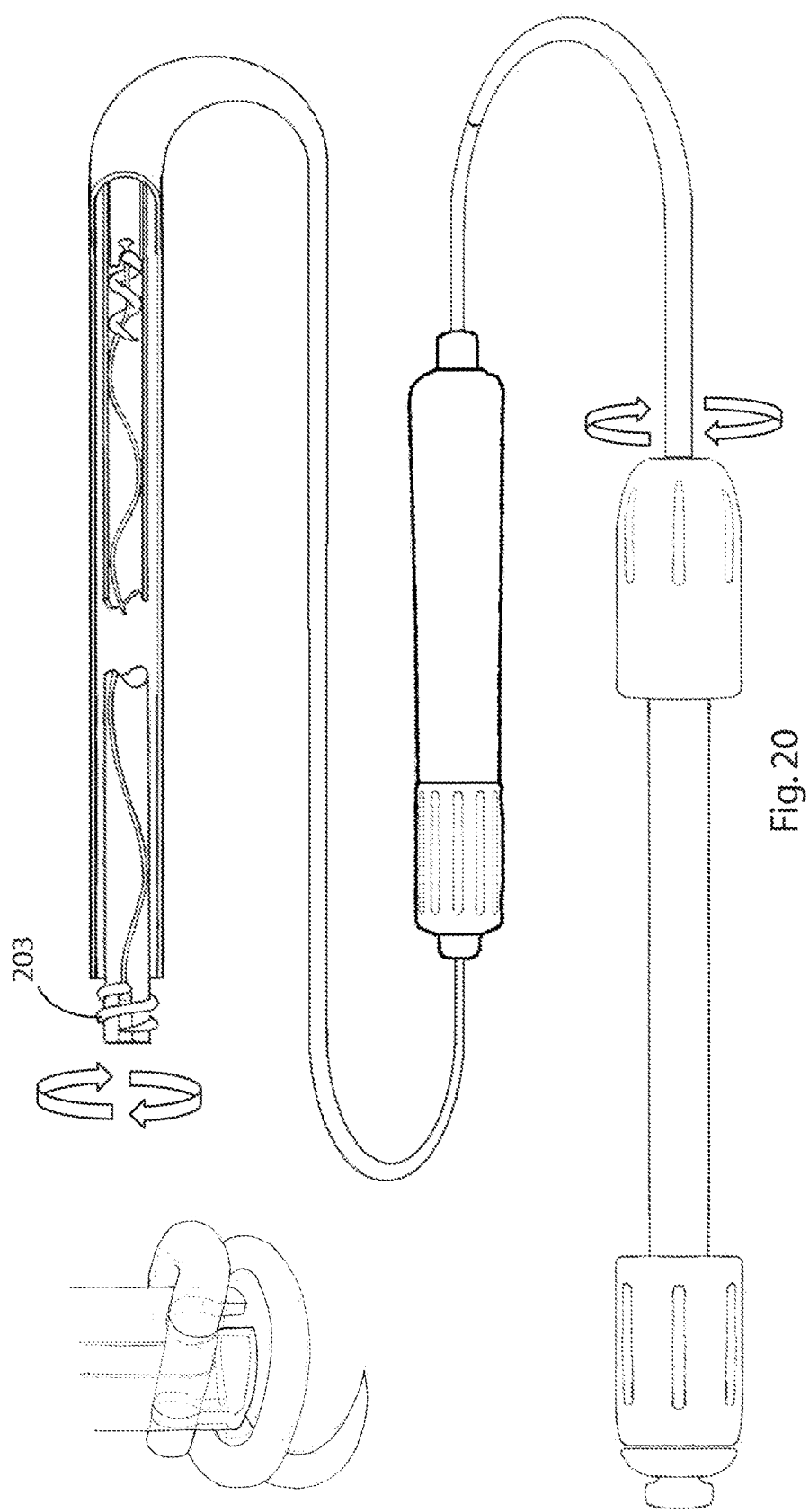
FIG. 20 is a partly sectional view of the delivery device of FIG. 17 showing the outer sheath partly retracted and rotation of the delivery device to allow distal anchoring element embed itself in adjacent tissue.
Figure 21:
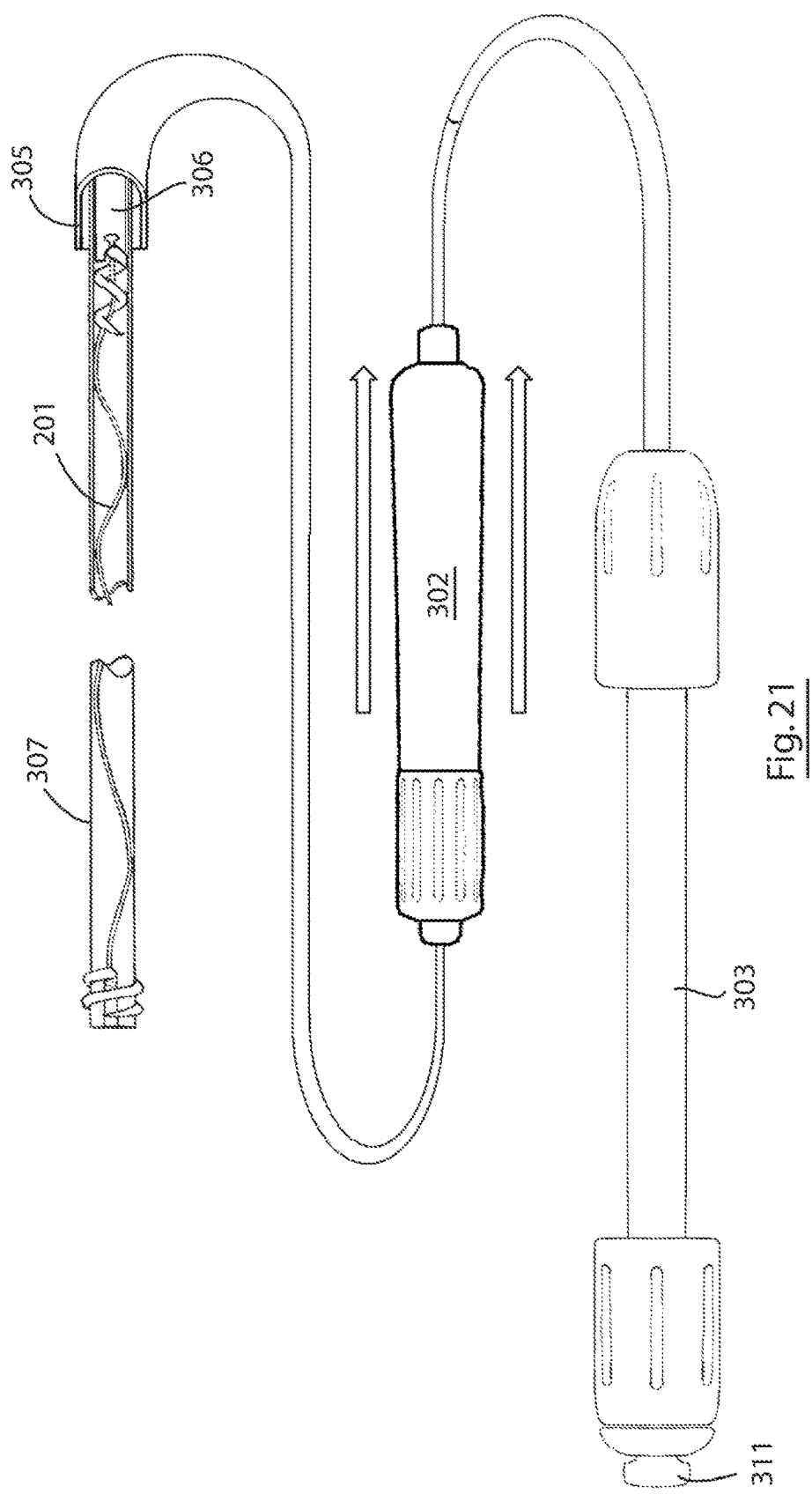
FIG. 21 is a partly sectional view of the delivery device of FIG. 17 showing the outer sheath fully retracted and the distal anchoring element embedded in adjacent tissue.
Figure 22:
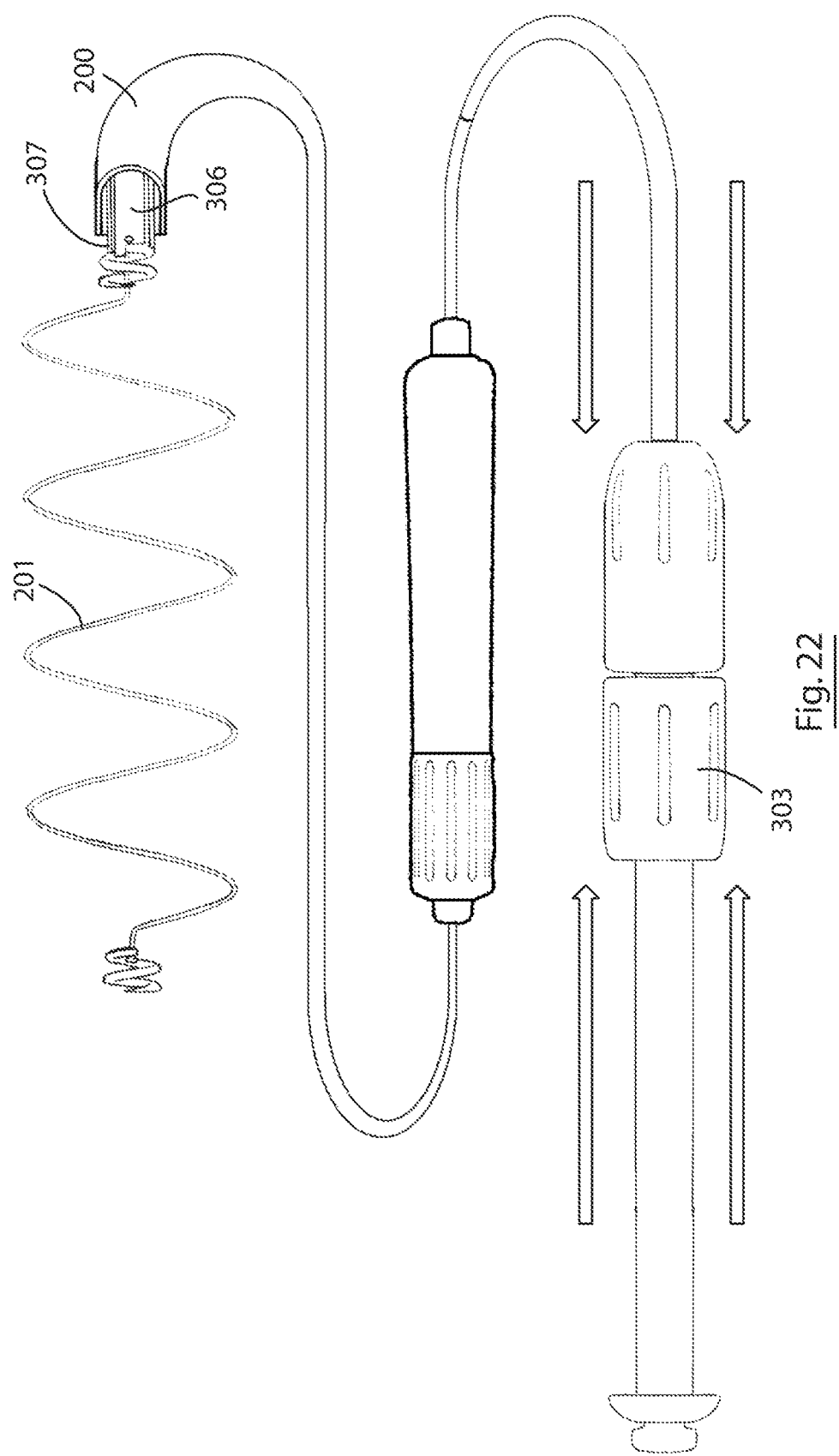
FIG. 22 is a partly sectional view of the delivery device of FIG. 17 showing the mid sheath fully retracted and the inner sheath advanced slightly to expose the proximal anchoring element.
Figures 25A, 25B, 25C:
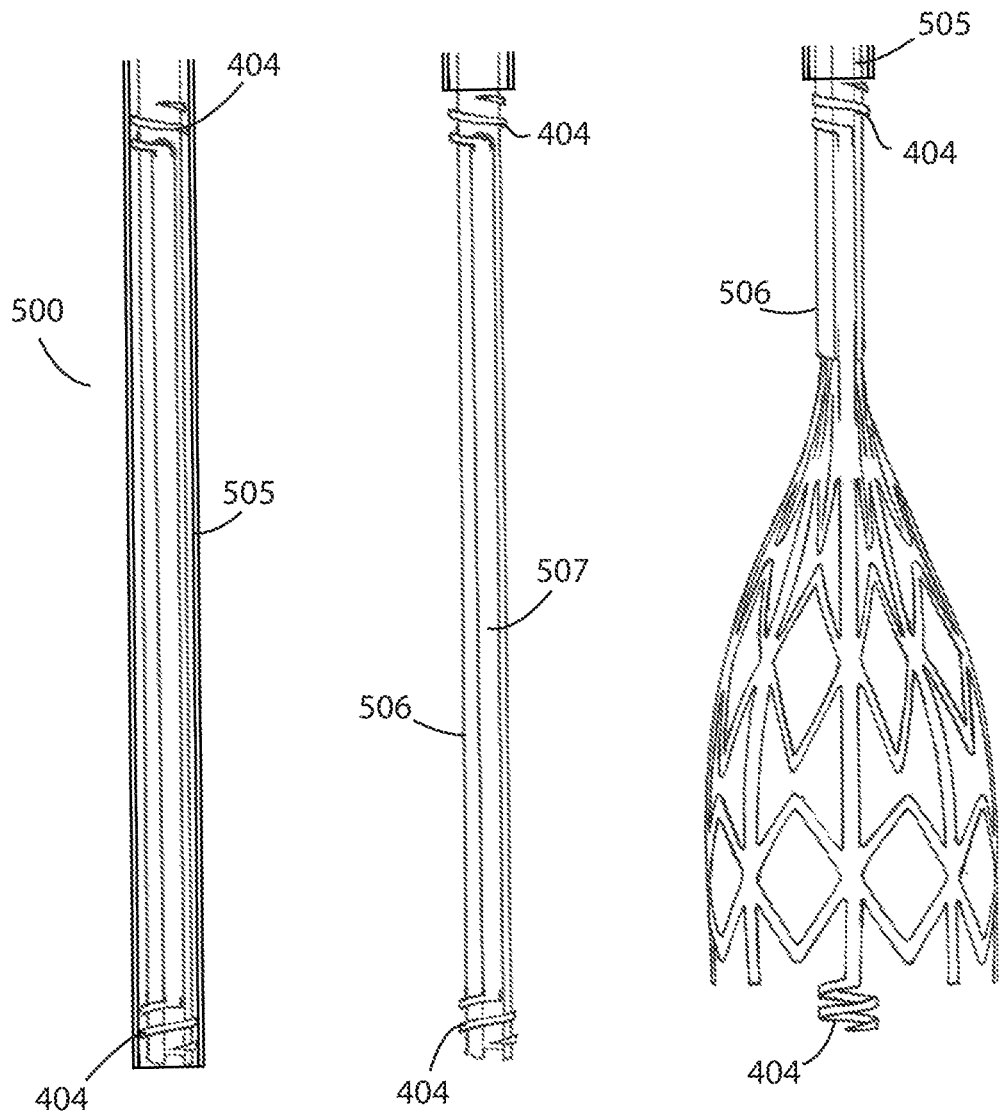
FIG. 25A is a sectional view of a delivery device of the invention configured for delivering an implantable intracardiac device of FIG. 24 and showing the device loaded into the delivery device and the outer sheath advanced.
FIG. 25B is a sectional view of the delivery device of FIG. 25A showing the outer sheath retracted exposing the distal and proximal anchoring elements.
FIG. 25C is a sectional view of the delivery device of FIG. 25A showing the mid sheath partially retracted and the implantable intracardiac device partially deployed.

Referring now to FIGS. 18 to 23, the use of the delivery device 300 to deliver the implantable intracardiac device 200 percutaneously to the left ventricle of the heart and anchoring it in position will be described in more detail. Referring to FIG. 18, the delivery device 300 is shown with the device 200 in-situ, with the proximal anchoring corkscrew 202 engaged with the distal end of the inner sheath 306, the distal anchoring corkscrew 203 engaged with the distal end of the mid sheath 307 and exposed on an outer surface of the mid sheath, and the coil stretched out within the mid sheath 307. In this delivery mode, the outer sheath 305 is fully extended fully covering the mid sheath, and the catheter 300 is extended along the right femoral vein into the heart until the distal end 304 is disposed in position within the left ventricle of the heath adjacent the LVOT septum and left ventricle mid septum. Referring to FIG. 19, the control handle element 302 is actuated as illustrated to partially retract the outer sheath 305 exposing the distal corkscrew anchor 203. Referring to FIG. 20, the catheter 300 is then rotated as illustrated to drive the anchor 203 into engagement with the adjacent tissue. Referring to FIG. 21, the outer sheath 305 is then fully retracted by actuation of the control handle element 302, and the distal anchor 203 is released from the mid sheath 307 by actuation of a button 311 on the control handle element 303. Referring to FIG. 22, the control handle element 303 is further actuated to fully withdraw the mid sheath 307, and the inner sheath 306 is slightly advanced as illustrated, exposing the coil 201 and proximal anchor 202. Referring to FIG. 23, the inner sheath 306 is rotated by actuation of the control handle element 303, driving the proximal anchor element 202 into engagement with adjacent tissue, and the catheter 300 is then retracted leaving the device in-situ in the left ventricle of the heart in a position to prevent systolic anterior motion of the mitral valve leaflet.

Referring to FIGS. 24A and 24B, there is illustrated an implantable intracardiac device according to the invention and indicated generally by the reference numeral 400 and comprising a blocking member formed of a generally cylindrical cage 401 having a proximal anchoring element 402 and distal anchoring element 403 formed at the ends of the cylindrical cage 401 and longitudinally aligned along a side of the cylindrical cage to enable engagement with tissue adjacent the blocking member. The cylindrical cage comprises longitudinal struts 405 and diamond shaped radial struts 406 connecting the longitudinal struts 405, the configuration allowing radial expansion of the device from a relaxed expanded configuration shown in FIG. 24A to a radially contracted configuration suitable for delivery in a delivery catheter. In more detail and referring to FIG. 24B, the distal anchoring element 403 comprises a corkscrew anchor 404 that is attached to, and extends away from, an end of a longitudinal strut 405 of the cylindrical cage and has a piercing tip 406 at a free end. Referring to FIG. 24A the proximal anchoring element 402 has a similar construction to the distal anchoring element.

Figure 26:
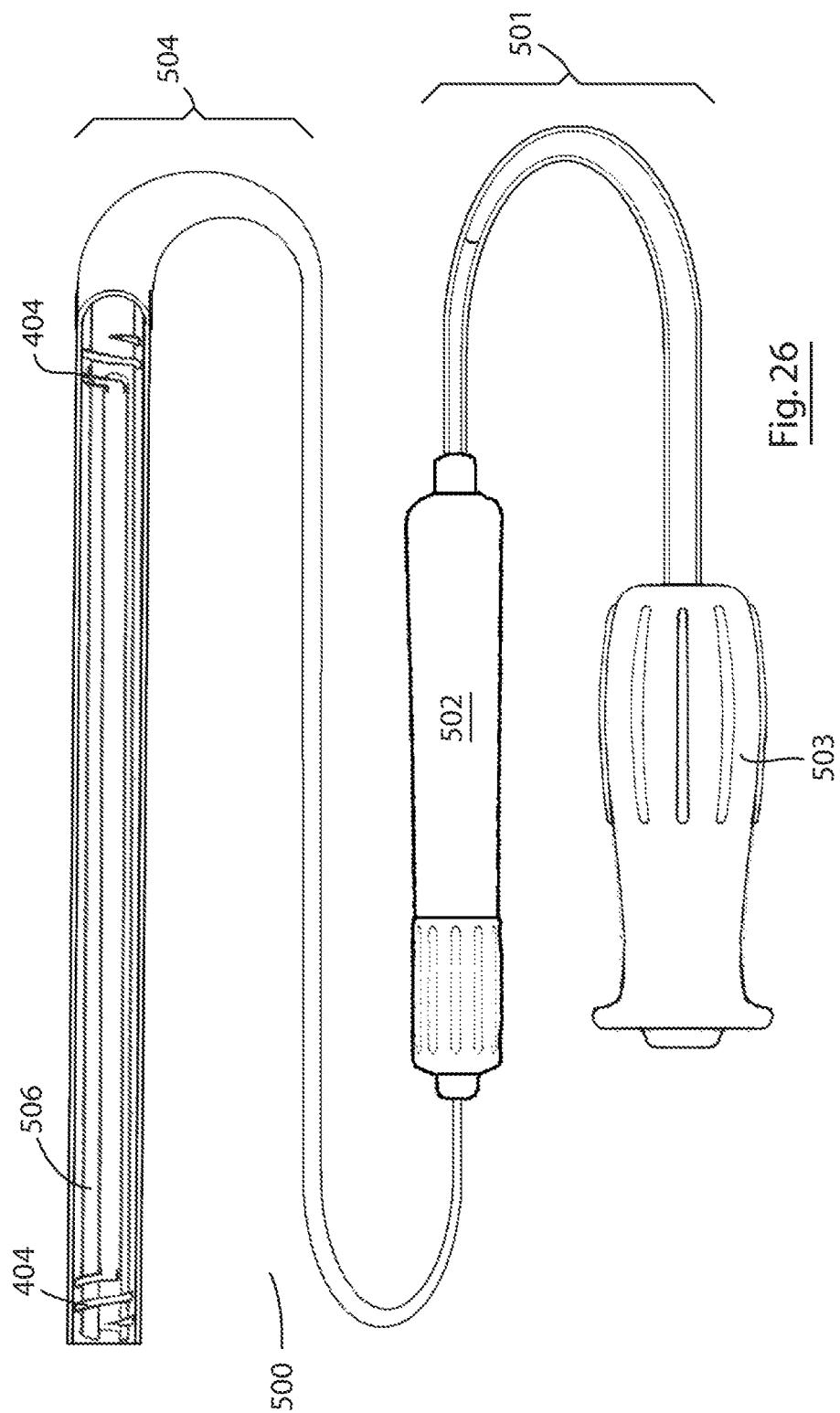
FIG. 26 is a partly sectional view of the delivery device of FIG. 24 showing the implantable intracardiac device in-situ within the device during delivery.

Referring to FIGS. 25-29, a delivery device for the implantable intracardiac device of FIG. 24, and it use in delivering the device into the left ventricle of the heart, is illustrated. Referring initially to FIG. 26, the delivery device comprises a catheter 500 having a distal end 501 with control handle elements 502, 503, and a proximal end 504 configured to receive the device 400. In more detail, and referring to FIGS. 25A to 25C, the distal end 504 of the catheter comprises an outer sheath 505 and an inner sheath 506. The inner sheath 506 comprises an elongated longitudinal slot 507 that has a length similar to the length of the device 400 when in a radially contracted configuration. The slot 507 allows the cylindrical mesh 401 (in a radially contracted configuration) to be threaded along the inside of the inner sheath 506 while the distal and proximal corkscrew anchors 404 are threaded along an outside of the inner sheath. The outer sheath 505 is movable from an extended position shown in FIG. 25A to a withdrawn position shown in FIG. 25B by actuation of the handle element 502, exposing the inner sheath 506 and distal and proximal corkscrew anchors 404. The inner sheath is movable from an extended position shown in FIG. 25B to a withdrawn position shown in FIG. 25C by actuation of the handle 503, releasing the device 400.

Referring now to FIGS. 26 to 29, the use of the catheter 500 to deliver the implantable intracardiac device 400 percutaneously to the left ventricle of the heart and anchoring it in position will be described in more detail. Referring to FIG. 26, the delivery device 500 is shown with the implantable intracardiac device 400 in-situ, with the proximal and distal anchoring corkscrews 404 spaced apart along the outside of the inner sheath 506, and the cylindrical mesh disposed within the inner sheath 506. In this delivery mode, the outer sheath 505 is fully extended fully covering the inner sheath 506, and the catheter 500 is extended along the right femoral vein into the heart until the distal end 504 is disposed in position within the left ventricle of the heath adjacent the LVOT septum and left ventricle mid septum. Referring to FIG. 27, the control handle element 502 is actuated as illustrated to fully retract the outer sheath 505 exposing the distal and proximal corkscrew anchors 404. Referring to FIG. 28, the catheter 500 is then rotated as illustrated to drive the two anchors 404 into engagement with the adjacent tissue. Referring to FIG. 29, the catheter 500 is then retracted which results in retraction of the inner sheath 506 allowing the cylindrical cage 401 expand and leaving the device in-situ in the left ventricle of the heart in a position to prevent systolic anterior motion of the mitral valve leaflet.

Referring to FIGS. 30A and B and 31A, B and C, there is illustrated an implantable intracardiac device according to an alternative embodiment of the invention, indicated generally by the reference numeral 600 and comprising a blocking member in the form of a helical coil 601, distal anchoring means in the form of a spaced apart co-axial helical coil 602 having a diameter smaller than the helical coil 601, and a stem 603 connecting the coils 601 and 602 that is at an angle to a longitudinal axis of the device. Referring to FIG. 30B, it can be seen that a proximal end 604 of the coil 601 projects slightly outside of the footprint of the coil 601 and likewise a distal end 605 of the coil 602 projects slightly outside of the footprint of the coil 602. The distal and proximal ends 604, 605 are provided with piercing tips. In use, the device is positioned in the left ventricle of the heart as previously described and the device is rotated to drive the coil 602 fully into engagement with adjacent tissue which approximates to about three full turns. The device is then further rotated to drive the proximal end 604 of coil 601 into the adjacent tissue.

Figure 32A:
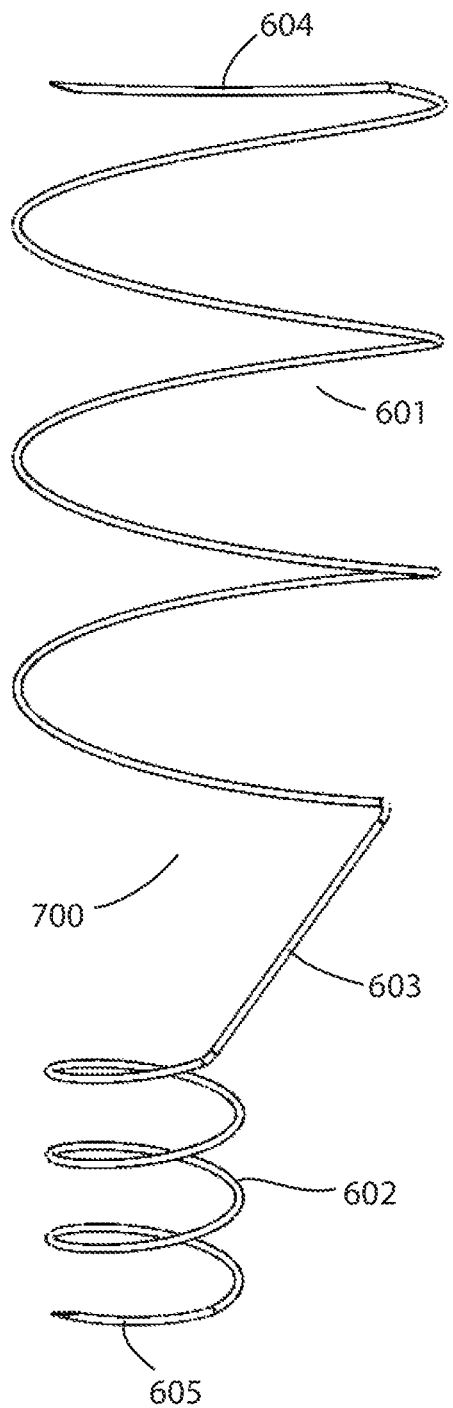
FIG. 32A is a front elevational view, 32B is a side elevational view, and 32C is a top elevation view of an implantable intracardiac device according to an alternative embodiment of the invention.
Figure 32B:
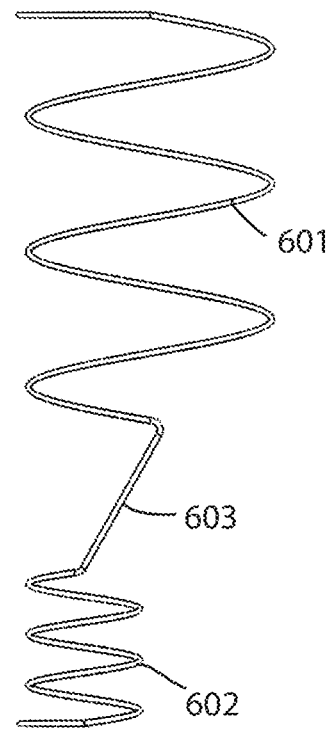
Figure 32C:
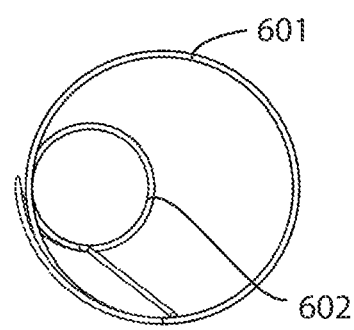
Figure 33A:
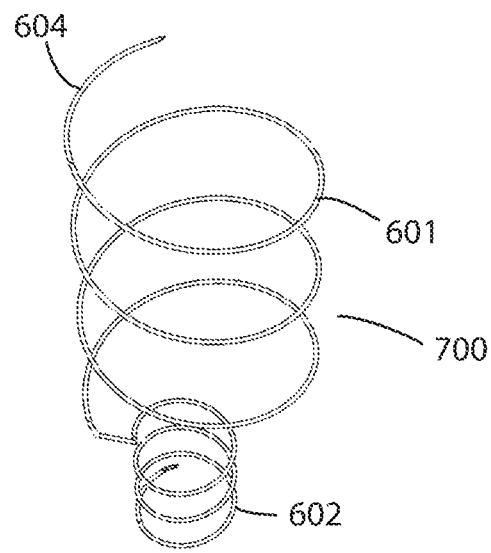
FIG. 33A is a front elevational view and 33B is a side elevational view of an implantable intracardiac device according to an alternative embodiment of the invention.
Figure 33B:
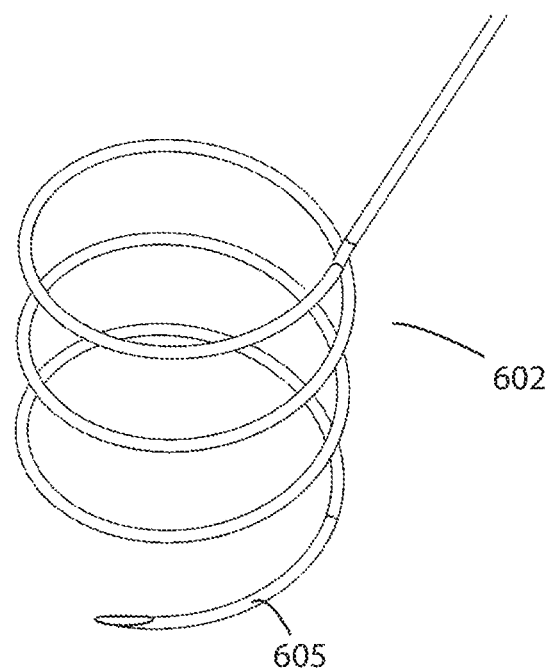

Referring to FIGS. 32A, B and C and FIGS. 33A, B and C, there is illustrated a further embodiment of the invention indicated generally by reference numeral 700 in which parts described with reference to the embodiment of FIGS. 30 and 31 are assigned the same reference numerals. In this embodiment, and referring specifically to FIG. 32C, the anchoring coil 602 is eccentrically disposed with respect to the blocking coil 601 with an edge of the coils overlapping in plain? view. The use of this embodiment is the same as that described with reference to the embodiment of FIGS. 30 and 31.

Figure 34A:
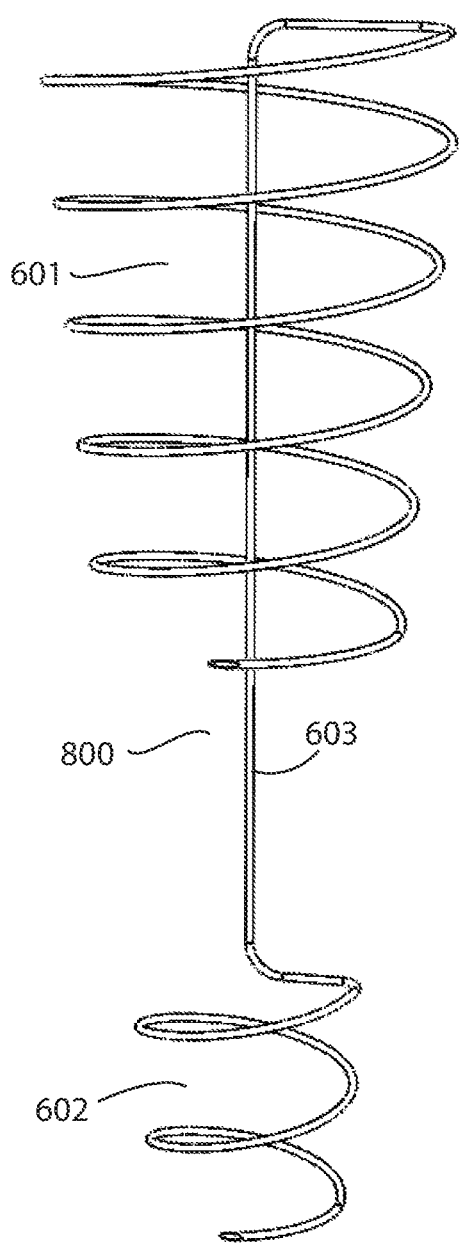
FIG. 34A is a front elevational view, 34B is a side elevational view, and 34C and 34D are top elevation views of an implantable intracardiac device according to an alternative embodiment of the invention.

Referring to FIGS. 34A, B, C and D, there is illustrated a further embodiment of the invention indicated generally by reference numeral 800 in which parts described with reference to the embodiment of FIGS. 30 and 31 are assigned the same reference numerals. In this embodiment, The anchoring coil 602 and blocking coil 601 are connected by a stem 603 that extends from a proximal end of the anchoring coil 602 up through a lumen of the blocking coil 601 and is attached to the blocking at a proximal end thereof. In addition, the blocking coil 601 tapers slightly towards a distal end thereof. The use of this embodiment is the same as that described with reference to the embodiment of FIGS. 30 and 31.

Figure 34C:
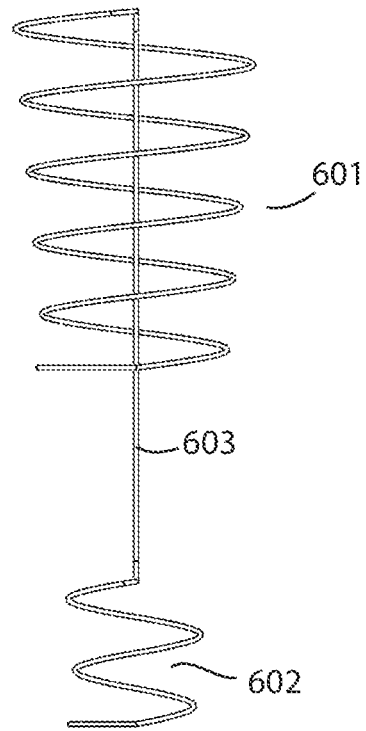
Figure 34D:
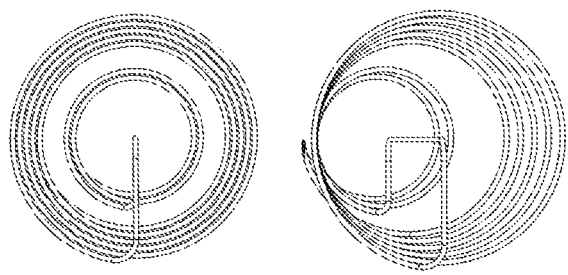
Figure 35A:
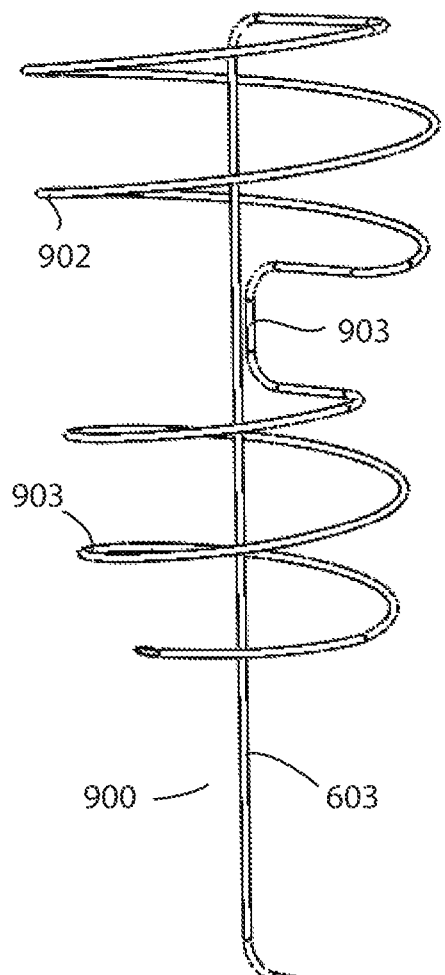
FIG. 35A is a front elevational view, 35B is a side elevational view, and 35C and 35D are top elevation views of an implantable intracardiac device according to an alternative embodiment of the invention.
Figure 35C:
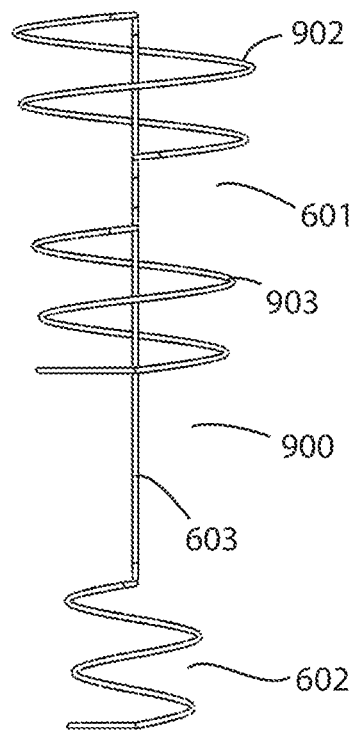
Figure 35D:
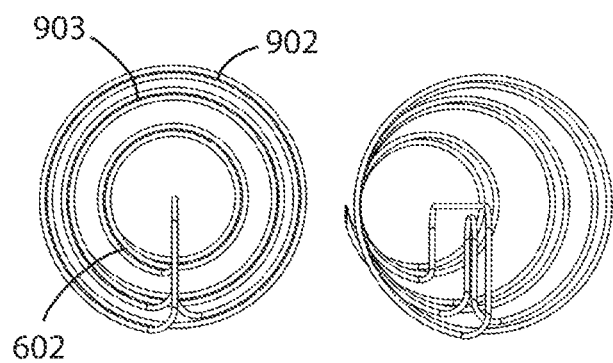

Referring to FIGS. 35A, B, C and D, there is illustrated a further embodiment of the invention indicated generally by reference numeral 900 in which parts described with reference to the embodiment of FIG. 34 are assigned the same reference numerals. In this embodiment, the blocking coil 601 comprises a proximal coil 902 and a distal coil 903 connected by a stem 903 that runs parallel to the stem 603. The use of this embodiment is the same as that described with reference to the embodiment of FIGS. 30 and 31.

Referring to FIGS. 36A, B, C and D, there is illustrated a further embodiment of the implantable intracardiac device of the invention indicated generally by reference numeral 1000 and comprising a cylindrical body 1001 formed of interconnected diagonal struts 1002. Three anchoring barbs 1003 are provided on a proximal end of the body at the end of struts, and an anchoring coil 1004 is provided at a distal end of the body 1001 and on the same side of the body as the anchoring barbs 1003. The provision of a cylindrical body formed of diagonal struts as opposed to a helical coil reduces the vertical deformation of the device in use.

Referring to FIGS. 37A, B, and C, there is illustrated a further embodiment of the implantable intracardiac device of the invention indicated generally by reference numeral 1100 and comprising a cylindrical body 1101 formed of series of interconnected loops 1102. One anchoring barb 1103 is provided on a proximal end of the body, and an anchoring coil 1104 is provided at a distal end of the body 1001 and on the same side of the body as the anchoring barbs 1003.

Figures 38A, 38B, 38C:
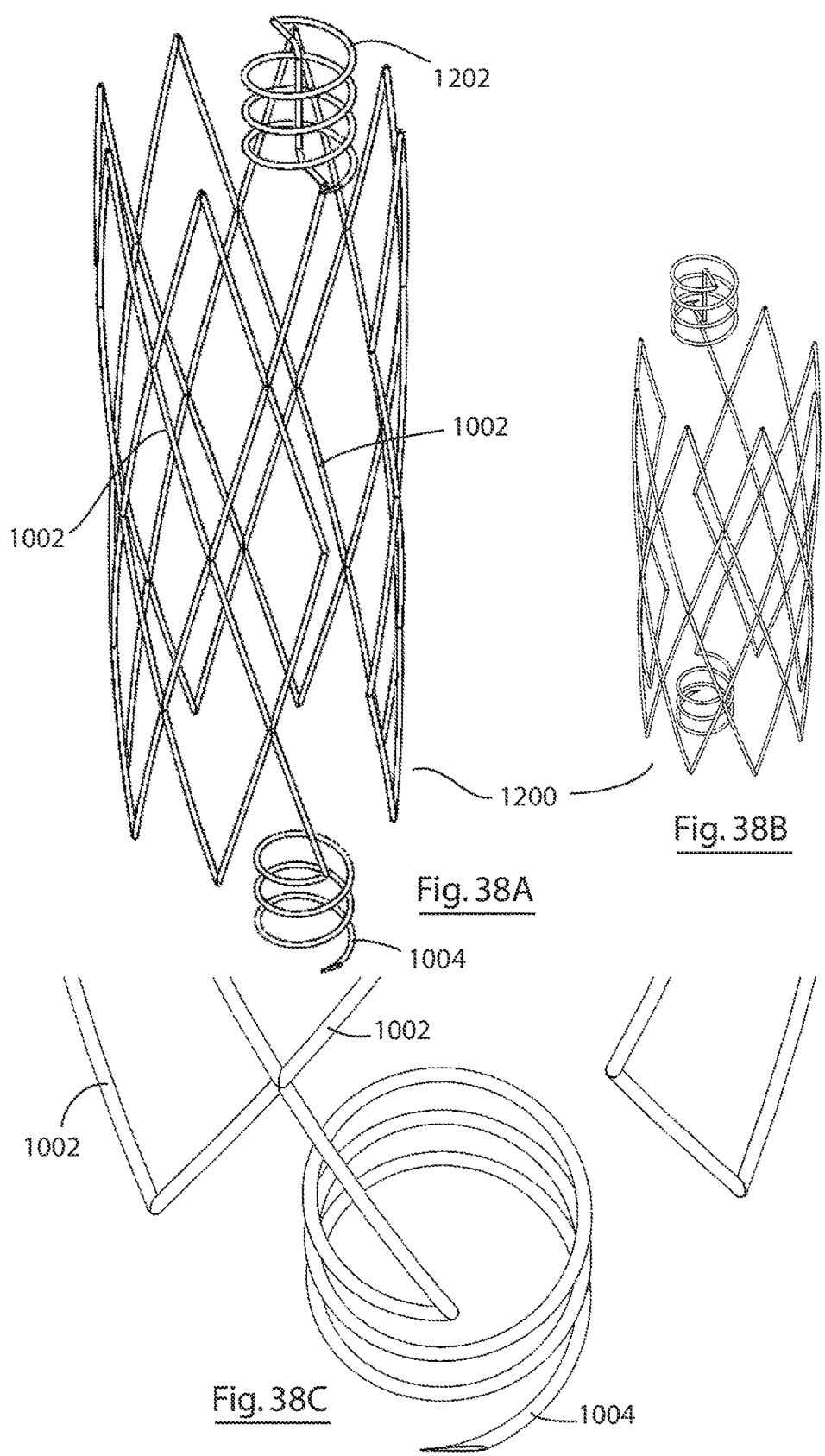
FIG. 38A is a front elevational view and 38B is a side elevational view of an implantable intracardiac device according to an alternative embodiment of the invention.
FIG. 38C is a detailed view of a distal end of the device of FIG. 38A.

Referring to FIGS. 38A, B, C and D, there is illustrated a further embodiment of the invention indicated generally by reference numeral 1200 in which parts described with reference to the embodiment of FIG. 36 are assigned the same reference numerals. In this embodiment, the proximal anchoring means are provided by an anchoring coil 1201.

Referring to FIGS. 39A, B and C, a further embodiment of the implantable intracardiac device of the invention is illustrated.

Deployment Procedure

The device is implanted in the cardiac catheterization lab while the patient is conscious.

Under local anesthetic, an 8F sheath is inserted in the right femoral vein.

The 8F sheath is then exchanged to a 71 cm deflectable sheath (e.g. Agilis SJM).

Via the right femoral vein, a transseptal approach is used to access the left ventricle (LV) with the deflectable sheath across the mitral valve.

(Alternatively, via the right femoral artery, the aortic valve is crossed retrogradely with a 0.032" guidewire, over which the deflectable sheath with the dilator is advanced to the left ventricle).

Once the LV cavity has been accessed with the actively deflectable delivery sheath, the following steps are pursued.
1. The distal anchoring active fixation screw is inserted in the mid septum.
2. After the above step the device is advanced out of the delivery sheath and self-expands to a diameter of 2 cm and a length of 2.5 cm.
3. After fixation of the distal end and after advancement of the device, the proximal anchoring active fixation screw is then inserted in the LVOT septum.

Upon completion of the above 3 deployment steps, the delivery sheath is removed.

The patient is anticoagulated with heparin during the procedure and for 24 hours post procedure and discharged home 24 hours post procedure on dual antiplatelet therapy (e.g. aspirin and clopidogrel) for three months (as is currently performed in patients undergoing mitral annuloplasty ring implantation, LA appendage closure device implantation, ASD and VSD closure device implantation procedures).

Retrieval Procedure

To engage the device from the leg requires:

Introduction of a snare to LV via a deflectable sheath (e.g. Agilis)

Proximal end of device is snared and slid back along the device to proximal anchoring active fixation screw beyond the crimping zone (relying on the crimping zone to provide tolerance to torque at the other end of the device)

The snare is then tightened and clocked counter-clockwise to disengage the proximal active fixation screw from the LVOT septum The snare is then loosened and slid down along the device to the distal anchoring active fixation screw The snare is then (again) tightened and clocked counter-clockwise to disengage the distal active fixation screw from the mid-septum The snare is then left on the device and the device is then retracted and retrieved into a deflectable sheath (e.g. Agilis—the same sheath that is used to deliver the device The surface material of the device is smooth and polished (unlike a pacemaker or ICD lead) and thereby not prone to friction or to adhesive fibrous sheath formation.

A lead locking stylet or laser extraction system should not be required.

Alternatively the device may be retracted once grabbed by a retrieval wire and the screws removed by direct traction using flexibility of screw material without being unscrewed (this is currently often necessary with pacemaker lead extraction whereby it may not be possible to advance a stylet to the distal fixation screw or to transmit counter-clockwise torque to the distal screw).

Alternatively a docking loop is available as an engagement site for a retrieval catheter at the base of each active fixation screw.

Advantages of Anti-SAM Device and Method of the Invention

An implantable endocardial device therapy for SAM in HOCM:

Obviates the requirement for surgical myectomy or alcohol septal ablation in HOCM patients with SAM.

Avoid the creation of myocardial scar as occurs in alcohol septal ablation and thereby have a lower risk of pro-arrhythmia.

The efficacy of the device can be assessed acutely in real time during implantation to ensure optimal sizing and deployment.

The radial force required of such a device is low as it only needs to overcome the Venturi effect of the left ventricular outflow tract (LVOT).

Prevents both LVOT obstruction and also prevents mitral regurgitation secondary to SAM.

Advantages Over Surgical Myectomy:

The Anti-SAM device is easily deployed and the threshold for intervention would therefore be less than for a surgical myectomy which requires open heart surgery and cardiopulmonary bypass. Surgical myectomy also carries a risk of causing a VSD which is avoided by the device.

The Anti-SAM device also obviates the requirement for papillary muscle reinsertion and mitral annuloplasty which is often performed concomitantly with a surgical myectomy.

Advantages Over TASH:

The device carries a lower risk to the patient than inducing a myocardial infarction with alcohol (TASH procedure) and carries a lower risk of causing complete AV conduction block and permanent pacemaker requirement.

The invention claimed is:

1. A method of preventing or inhibiting systolic anterior motion of the anterior mitral valve leaflet in a mammal, comprising:
   inserting and positioning an implantable intracardiac device, having a blocking member and at least one anchoring element, within the left ventricle of the heart, and at least partially within the left ventricular outflow tract of the mammal; and
   coupling the anchoring element to a wall of the left ventricle,
   wherein when the intracardiac device is inserted, the blocking member blocks systolic anterior motion of the anterior mitral valve leaflet into the left ventricular outflow tract without re-shaping of the mitral valve annulus.

2. The method of claim 1, wherein the coupling of the anchoring element includes coupling the anchoring element to the interventricular septum.

3. The method of claim 1, wherein
   the anchoring element is a first anchoring element,
   the device further comprises a second anchoring element, and
   the method further comprises coupling the second anchoring element to a wall of the left ventricle.

4. The method of claim 1, wherein
   the anchoring element is a first anchoring element disposed on a proximal end of the device,
   the device includes a second anchoring element disposed on a distal end of the device, and
   the method further comprises coupling the first and second anchoring elements to the interventricular septum of the heart.

5. The method of claim 1, wherein the implantable intracardiac device is inserted into the left ventricle of the heart percutaneously and transluminally.

6. The method of claim 1, wherein the implantable intracardiac device is inserted into the left ventricle:
   (1) via the right femoral artery and retrogradely across the aortic valve; or
   (2) via the right femoral vein and transseptally.

7. The method of claim 1, wherein the blocking member comprises a coil-shaped body.

8. A method of preventing or inhibiting systolic anterior motion of the anterior mitral valve leaflet in a mammal, comprising:
   inserting and positioning an implantable intracardiac device, having a blocking member and at least one anchoring element, within the left ventricle of the heart, and at least partially within the left ventricular outflow tract of the mammal; and
   fixing the anchoring element to a wall of the left ventricle,
   wherein when the intracardiac device is inserted, the blocking member contacts the anterior mitral valve leaflet during motion of the anterior mitral valve leaflet without re-shaping of the mitral valve annulus.

9. The method of claim 8, wherein the fixing of the anchoring element includes fixing the anchoring element to the interventricular septum.

10. The method of claim 8, wherein
    the anchoring element is a first anchoring element,
    the device further comprises a second anchoring element, and
    the method further comprises fixing the second anchoring element to a wall of the left ventricle.

11. The method of claim 8, wherein
    the anchoring element is a first anchoring element disposed on a proximal end of the device,
    the device includes a second anchoring element disposed on a distal end of the device, and
    the method further comprises fixing the first and second anchoring elements to the interventricular septum of the heart.

12. The method of claim 8, wherein the implantable intracardiac device is inserted into the left ventricle of the heart percutaneously and transluminally.

13. The method of claim 8, wherein the implantable intracardiac device is inserted into the left ventricle:
    (1) via the right femoral artery and retrogradely across the aortic valve; or
    (2) via the right femoral vein and transseptally.

14. The method of claim 8, wherein the mammal is a human.

15. The method of claim 8, wherein the blocking member comprises a coil-shaped body.

16. A method of preventing or inhibiting systolic anterior motion of the anterior mitral valve leaflet in a mammal, comprising:
    inserting and positioning an implantable intracardiac device, having a blocking member and at least one anchoring element, within the left ventricle of the heart, and at least partially within the left ventricular outflow tract of the mammal; and
    fixing the anchoring element into a wall of the interventricular septum,
    wherein when the intracardiac device is inserted, the blocking member is located in the path of systolic anterior motion of the anterior mitral valve leaflet in the left ventricular outflow tract, and reduces systolic anterior motion of the anterior mitral valve leaflet without compressing the mitral valve annulus.

17. The method of claim 16, wherein
    the anchoring element is a first anchoring element,
    the device further comprises a second anchoring element, and
    the method further comprises fixing the second anchoring element to a wall of the left ventricle.

18. The method of claim 16, wherein
the anchoring element is a first anchoring element disposed on a proximal end of the device,
the device includes a second anchoring element disposed on a distal end of the device, and
the method further comprises coupling the first and second anchoring elements to the interventricular septum of the heart.

19. The method of claim 16, wherein the blocking member comprises a coil-shaped body.

20. The method of claim 1, wherein the mammal is:
a mammal suffering from left ventricular outflow tract (LVOT) obstruction,
a mammal suffering from hypertrophic obstructive cardiomyopathy (HOCM),
a mammal who has had mitral valve surgical annuloplasty, or
a mammal having a sigmoid intraventricular septum with symptomatic outflow tract obstruction.

21. The method of claim 8, wherein the mammal is:
a mammal suffering from left ventricular outflow tract (LVOT) obstruction,
a mammal suffering from hypertrophic obstructive cardiomyopathy (HOCM),
a mammal who has had mitral valve surgical annuloplasty, or
a mammal having a sigmoid intraventricular septum with symptomatic outflow tract obstruction.

22. The method of claim 16, wherein the mammal is:
a mammal suffering from left ventricular outflow tract (LVOT) obstruction,
a mammal suffering from hypertrophic obstructive cardiomyopathy (HOCM),
a mammal who has had mitral valve surgical annuloplasty, or
a mammal having a sigmoid intraventricular septum with symptomatic outflow tract obstruction.

* * * * *